(12) United States Patent
Kotenko et al.

(10) Patent No.: US 11,352,404 B2
(45) Date of Patent: Jun. 7, 2022

(54) PHOSPHATIDYLSERINE TARGETING FUSION MOLECULES AND METHODS FOR THEIR USE

(71) Applicant: RUTGERS, THE STATE UNIVERSITY OF NEW JERSEY, New Brunswick, NJ (US)

(72) Inventors: Sergei V. Kotenko, East Brunswick, NJ (US); Raymond B. Birge, New York, NY (US); Viralkumar Rameshkumar Davra, Keasbey, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 16/631,961

(22) PCT Filed: Jul. 24, 2018

(86) PCT No.: PCT/US2018/043357
§ 371 (c)(1),
(2) Date: Jan. 17, 2020

(87) PCT Pub. No.: WO2019/023156
PCT Pub. Date: Jan. 31, 2019

(65) Prior Publication Data
US 2020/0181221 A1    Jun. 11, 2020

Related U.S. Application Data

(60) Provisional application No. 62/536,107, filed on Jul. 24, 2017.

(51) Int. Cl.
*C07K 19/00*        (2006.01)
*C07K 14/555*      (2006.01)
(Continued)

(52) U.S. Cl.
CPC ............ *C07K 14/555* (2013.01); *A61P 35/00* (2018.01); *C07K 14/71* (2013.01); *A61K 38/00* (2013.01); *C07K 2319/033* (2013.01)

(58) Field of Classification Search
None
See application file for complete search history.

(56) References Cited

U.S. PATENT DOCUMENTS 6,211,142 B1    4/2001  Hammonds et al.
6,312,694 B1   11/2001  Thorpe et al.
(Continued)

FOREIGN PATENT DOCUMENTS

| CA | 2909669 | 4/1916 |
|---|---|---|
| JP | 4743672 | 5/2011 |

(Continued)

OTHER PUBLICATIONS

Lew et al.,Differential TAM receptor-ligand-phospholipid interactions delimit differential TAM bioactivities, eLIFE, 2014;3:e03385, DOI: 10.7554/eLife.03385 Sep. 2014.*

(Continued)

*Primary Examiner* — Claire Kaufman
(74) *Attorney, Agent, or Firm* — Licata & Tyrrell P.C.

(57) ABSTRACT

Fusion molecules of a cytokine or portion thereof and a polypeptide which targets the fusion protein to phosphatidylserine, pharmaceutical compositions thereof, and methods for their use in targeting a cytokine or portion thereof to a pathological site and treating a disease or condition responsive to cytokine treatment are provided.

10 Claims, 15 Drawing Sheets

Specification includes a Sequence Listing.

(51) Int. Cl.
*A61P 35/00* (2006.01)
*C07K 14/71* (2006.01)
*A61K 38/00* (2006.01)

(56) References Cited

U.S. PATENT DOCUMENTS

| | | | |
|---|---|---|---|
| 8,486,391 | B2 | 7/2013 | Thorpe et al. |
| 8,709,430 | B2 | 4/2014 | Thorpe et al. |
| 8,956,616 | B2* | 2/2015 | Thorpe .................. A61P 5/14 424/178.1 |
| 2002/0193569 | A1 | 12/2002 | Hanna |
| 2015/0210743 | A1 | 7/2015 | Garred et al. |
| 2016/0168269 | A1* | 6/2016 | Nielsen .............. A61K 47/6811 424/134.1 |
| 2016/0311886 | A1 | 10/2016 | Thorpe et al. |
| 2016/0367695 | A1* | 12/2016 | Wilson .................. C07K 14/57 |
| 2017/0073388 | A1 | 3/2017 | Grewal et al. |

FOREIGN PATENT DOCUMENTS

| | | |
|---|---|---|
| JP | 5478285 | 2/2014 |
| WO | 2012/064658 | 5/2012 |
| WO | 2014/151535 | 9/2014 |

OTHER PUBLICATIONS

Park et al., The Axl/Gas6 pathway is required for optimal cytokine signaling during human natural killer cell development, Blood, 113:2470-2477, 2009.*

Tsou et al., Receptor tyrosine kinases, TYRO3, AXL, and MER, demonstrate distinct patterns and complex regulation of ligand-induced activation, J. Biol. Chem. 289(37):25750-63, Sep. 2014.*

Beck et al. "Combination of a Monoclonal Anti-Phosphatidylserine Antibody With Gemcitabine Strongly Inhibits the Growth and Metastasis of Orthotopic Pancreatic Tumors in Mice" Int. J. Cancer 2005 118:2639-2643.

Birge et al. "Phosphatidylserine is a Global Immunosuppressive Signal in Efferocytosis, Infectious Disease, and Cancer" Cell Death and Differentiation 2016 23:962-978.

Chalassani et al. "A Phase I Clinical Trial of Bavituximab and Paclitaxel in Patients With HER2 Negative Metastatic Breast Cancer" Cancer Med. 2015 4:1051-1059.

De Freitas Balanco et al. "Apoptotic Mimicry by an Obligate Intracellular Parasite Downregulates Macrophage Microbicidal Activity" Curr. Biol. 2001 11:1870-1873.

DeRose et al. "Development of Bavituximab, a Vascular Targeting Agent With Immune-Modulating Properties, for Lung Cancer Treatment" Immunotherapy 2011 3:933-944 (Abstract only).

Digumarti et al. "Bavituximab Plus Paclitaxel and Carboplatin for the Treatment of Advanced Non-Small-Cell Lung Cancer" Lung Cancer 2014 86:231-236.

Dowall et al. "Effective Binding of a Phosphatidylserine-Targeting Antibody to Ebola Virus Infected Cells and Purified Virions" J. Immunol. Res. 2015 347903 9 pages.

Gerber et al. "Clin. Phase I Safety and Pharmacokinetic Study of Bavituximab, a Chimeric Phosphatidylserine-Targeting Monoclonal Antibody, in Patients With Advanced Solid Tumors" Cancer Res. 2011 17:6888-6896.

He et al. "Antiphosphatidylserine Antibody Combined With Irradiation Damages Tumor Blood Vessels and Induces Tumor Immunity in a Rat Model of Glioblastoma" Clin. Cancer Res. 2009 15: 6871-6880.

Huang et al. "A Monoclonal Antibody That Binds Anionic Phospholipids on Tumor Blood Vessels Enhances the Antitumor Effect of Docetaxel on Human Breast Tumors in Mice" Cancer Res. 2005 65:4408-4416.

Huang et al. "Inhibition of tumor growth by targeting cytokines to the inside-out phosphatidylserine (PS) on tumor vascular endothelium with 2aG4" Abstract 3539 AACR Annual Meeting Apr. 14-18, 2007 Canc. Res. 6(9) Suppl. 2007.

Huynh et al. "Phosphatidylserine-dependent Ingestion of Apoptotic Cells Promotes TGF-beta1 Secretion and the Resolution of Inflammation" J. Clin. Invest. 2002 109:41-50.

Kasikara et al. "Phosphatidylserine Sensing by TAM Receptors Regulates AKT-Dependent Chemoresistance and PD-L1 Expression" Molecular Cancer Research 2017 15(6):753-64.

Kimani et al. "Small Molecule Inhibitors Block Gas6-inducible TAM Activation and Tumorigenicity" Scientific Reports 2017 7:43908.

Linger et al. "TAM Receptor Tyrosine Kinases: Biologic Functions, Signaling, and Potential Therapeutic Targeting in Human Cancer" Advances in Cancer Research 2008 100:35-83.

Rajotte et al. "Gas6-mediated signaling is dependent on the engagement of its gamma-carboxyglutamic acid domain with phosphatidylserine" Biochemical and Biophysical Research Communications 2008 376:70-73.

Ran et al. "Increased Exposure of Anionic Phospholipids on the Surface of Tumor Blood Vessels" Cancer Res. 2002 62:6132-6140.

Rothlin et al. "TAM Receptors are Pleiotropic Inhibitors of the Innate Immune Response" Cell 2007 131: 1124-1136.

Soares et al. "Targeting Inside-Out Phosphatidylserine as a Therapeutic Strategy for Viral Diseases" Nat. Med. 2008 14 (12): 1357-1362.

globenewswire.com/news-release/2017/06/05/1008110/0/en/Peregrine-Pharmaceuticals-Presents-Preliminary-Correlative-Analysis-of-PD-L1-Expression-from-SUNRISE-Trial-at-ASCO-2017.html Jun. 5, 2017.

Search Report and Written Opinion in PCT/US2018/043357 dated Oct. 15, 2018.

Preliminary Report on Patentabiliy in PCT/US2018/043357 dated Jan. 28, 2020.

Extended European Search Report in Patent Application No. 18837567.9 dated Jul. 9, 2020.

* cited by examiner

FIG. 9

| TARGETING MOLECULE | PS TARGETING ANTI-TUMOR ACTIVITY | OFF-TARGET ADVERSE EFFECTS | TUMOR SPECIFIC IMMUNITY |
|---|---|---|---|
| IFN-λ2 | ✗ | ✓ | ✗ |
| IFN-β | ✗ | ✓ | ✗ |
| IFN-β-IFN-λ2 | ✗ | ✓ | ✗ |
| GAS6 (GLA)-IFN-λ2 | ✓ | ✗ | ✓ |
| GAS6 (GLA)-IFN-β | ✓ | ✗ | ✓ |
| GAS6 (GLA)-IFN-β-IFN-λ2 | ✓ | ✗ | ✓ |
| GAS6 (GLA+EGF)-IFN-λ2 | ✓ | ✗ | ✓ |
| GAS6 (GLA+EGF)-IFN-β | ✓ | ✗ | ✓ |
| GAS6 (GLA+EGF)-IFN-β-IFN-λ2 | ✓ | ✗ | ✓ |

SEQUENCE LISTING

```
<160> NUMBER OF SEQ ID NOS: 50

<210> SEQ ID NO 1
<211> LENGTH: 91
<212> TYPE: PRT
<213> ORGANISM: Mus musculus

<400> SEQUENCE: 1

Met Pro Pro Pro Pro Gly Pro Ala Ala Ala Leu Gly Thr Ala Leu Leu
1               5                   10                  15

Leu Leu Leu Leu Ala Ser Glu Ser Ser His Thr Val Leu Leu Arg Ala
                20                  25                  30

Arg Glu Ala Ala Gln Phe Leu Arg Pro Arg Gln Arg Arg Ala Tyr Gln
            35                  40                  45

Val Phe Glu Glu Ala Lys Gln Gly His Leu Glu Arg Glu Cys Val Glu
        50                  55                  60

Glu Val Cys Ser Lys Glu Glu Ala Arg Glu Val Phe Glu Asn Asp Pro
65                  70                  75                  80

Glu Thr Glu Tyr Phe Tyr Pro Arg Tyr Gln Glu
                85                  90

<210> SEQ ID NO 2
<211> LENGTH: 65
<212> TYPE: PRT
<213> ORGANISM: Mus musculus

<400> SEQUENCE: 2

Thr Val Leu Leu Arg Ala Arg Glu Ala Ala Gln Phe Leu Arg Pro Arg
1               5                   10                  15

Gln Arg Arg Ala Tyr Gln Val Phe Glu Glu Ala Lys Gln Gly His Leu
                20                  25                  30

Glu Arg Glu Cys Val Glu Glu Val Cys Ser Lys Glu Glu Ala Arg Glu
            35                  40                  45

Val Phe Glu Asn Asp Pro Glu Thr Glu Tyr Phe Tyr Pro Arg Tyr Gln
```

Glu
65

<210> SEQ ID NO 3
<211> LENGTH: 46
<212> TYPE: PRT
<213> ORGANISM: Mus musculus

<400> SEQUENCE: 3

Ala Tyr Gln Val Phe Glu Glu Ala Lys Gln Gly His Leu Glu Arg Glu
1               5                   10                  15

Cys Val Glu Glu Val Cys Ser Lys Glu Glu Ala Arg Glu Val Phe Glu
            20                  25                  30

Asn Asp Pro Glu Thr Glu Tyr Phe Tyr Pro Arg Tyr Gln Glu
        35                  40                  45

<210> SEQ ID NO 4
<211> LENGTH: 94
<212> TYPE: PRT
<213> ORGANISM: Homo sapien

<400> SEQUENCE: 4

Met Ala Pro Ser Leu Ser Pro Gly Pro Ala Ala Leu Arg Arg Ala Pro
1               5                   10                  15

Gln Leu Leu Leu Leu Leu Leu Ala Ala Glu Cys Ala Leu Ala Ala Leu
            20                  25                  30

Leu Pro Ala Arg Glu Ala Thr Gln Phe Leu Arg Pro Arg Gln Arg Arg
        35                  40                  45

Ala Phe Gln Val Phe Glu Glu Ala Lys Gln Gly His Leu Glu Arg Glu
    50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp
                85                  90

<210> SEQ ID NO 5
<211> LENGTH: 64
<212> TYPE: PRT
<213> ORGANISM: Homo sapien

<400> SEQUENCE: 5

Ala Leu Leu Pro Ala Arg Glu Ala Thr Gln Phe Leu Arg Pro Arg Gln
1               5                   10                  15

Arg Arg Ala Phe Gln Val Phe Glu Glu Ala Lys Gln Gly His Leu Glu
            20                  25                  30

Arg Glu Cys Val Glu Glu Leu Cys Ser Arg Glu Glu Ala Arg Glu Val
        35                  40                  45

Phe Glu Asn Asp Pro Glu Thr Asp Tyr Phe Tyr Pro Arg Tyr Leu Asp
    50                  55                  60

<210> SEQ ID NO 6
<211> LENGTH: 46
<212> TYPE: PRT
<213> ORGANISM: Homo sapien

<400> SEQUENCE: 6

Ala Phe Gln Val Phe Glu Glu Ala Lys Gln Gly His Leu Glu Arg Glu
1               5                   10                  15

```
Cys Val Glu Glu Leu Cys Ser Arg Glu Ala Arg Glu Val Phe Glu
            20                  25                  30

Asn Asp Pro Glu Thr Asp Tyr Phe Tyr Pro Arg Tyr Leu Asp
            35                  40                  45
```

<210> SEQ ID NO 7
<211> LENGTH: 87
<212> TYPE: PRT
<213> ORGANISM: Homo sapien

<400> SEQUENCE: 7

```
Met Arg Val Leu Gly Gly Arg Cys Gly Ala Leu Leu Ala Cys Leu Leu
1               5                   10                  15

Leu Val Leu Pro Val Ser Glu Ala Asn Phe Leu Ser Lys Gln Gln Ala
            20                  25                  30

Ser Gln Val Leu Val Arg Lys Arg Ala Asn Ser Leu Leu Glu Glu
            35                  40                  45

Thr Lys Gln Gly Asn Leu Glu Arg Glu Cys Ile Glu Glu Leu Cys Asn
    50                  55                  60

Lys Glu Glu Ala Arg Glu Val Phe Glu Asn Asp Pro Glu Thr Asp Tyr
65                  70                  75                  80

Phe Tyr Pro Lys Tyr Leu Val
                85
```

<210> SEQ ID NO 8
<211> LENGTH: 63
<212> TYPE: PRT
<213> ORGANISM: Homo sapien

<400> SEQUENCE: 8

```
Asn Phe Leu Ser Lys Gln Gln Ala Ser Gln Val Leu Val Arg Lys Arg
1               5                   10                  15

Arg Ala Asn Ser Leu Leu Glu Glu Thr Lys Gln Gly Asn Leu Glu Arg
            20                  25                  30

Glu Cys Ile Glu Glu Leu Cys Asn Lys Glu Glu Ala Arg Glu Val Phe
            35                  40                  45

Glu Asn Asp Pro Glu Thr Asp Tyr Phe Tyr Pro Lys Tyr Leu Val
    50                  55                  60
```

<210> SEQ ID NO 9
<211> LENGTH: 46
<212> TYPE: PRT
<213> ORGANISM: Homo sapien

<400> SEQUENCE: 9

```
Ala Asn Ser Leu Leu Glu Glu Thr Lys Gln Gly Asn Leu Glu Arg Glu
1               5                   10                  15

Cys Ile Glu Glu Leu Cys Asn Lys Glu Glu Ala Arg Glu Val Phe Glu
            20                  25                  30

Asn Asp Pro Glu Thr Asp Tyr Phe Tyr Pro Lys Tyr Leu Val
            35                  40                  45
```

<210> SEQ ID NO 10
<211> LENGTH: 184
<212> TYPE: PRT
<213> ORGANISM: Homo sapien

<400> SEQUENCE: 10

```
Cys Ile Asn Lys Tyr Gly Ser Pro Tyr Thr Lys Asn Ser Gly Phe Ala
1               5                   10                  15
```

```
Thr Cys Val Gln Asn Leu Pro Asp Gln Cys Thr Pro Asn Pro Cys Asp
                20                  25                  30

Arg Lys Gly Thr Gln Ala Cys Gln Asp Leu Met Gly Asn Phe Phe Cys
            35                  40                  45

Leu Cys Lys Ala Gly Trp Gly Gly Arg Leu Cys Asp Lys Asp Val Asn
    50                  55                  60

Glu Cys Ser Gln Glu Asn Gly Gly Cys Leu Gln Ile Cys His Asn Lys
65                  70                  75                  80

Pro Gly Ser Phe His Cys Ser Cys His Ser Gly Phe Glu Leu Ser Ser
                85                  90                  95

Asp Gly Arg Thr Cys Gln Asp Ile Asp Glu Cys Ala Asp Ser Glu Ala
            100                 105                 110

Cys Gly Glu Ala Arg Cys Lys Asn Leu Pro Gly Ser Tyr Ser Cys Leu
        115                 120                 125

Cys Asp Glu Gly Phe Ala Tyr Ser Ser Gln Glu Lys Ala Cys Arg Asp
130                 135                 140

Val Asp Glu Cys Leu Gln Gly Arg Cys Glu Gln Val Cys Val Asn Ser
145                 150                 155                 160

Pro Gly Ser Tyr Thr Cys His Cys Asp Gly Arg Gly Gly Leu Lys Leu
                165                 170                 175

Ser Gln Asp Met Asp Thr Cys Glu
                180

<210> SEQ ID NO 11
<211> LENGTH: 196
<212> TYPE: PRT
<213> ORGANISM: Homo sapien

<400> SEQUENCE: 11

Cys Leu Arg Ser Phe Gln Thr Gly Leu Phe Thr Ala Ala Arg Gln Ser
1               5                   10                  15

Thr Asn Ala Tyr Pro Asp Leu Arg Ser Cys Val Asn Ala Ile Pro Asp
                20                  25                  30

Gln Cys Ser Pro Leu Pro Cys Asn Glu Asp Gly Tyr Met Ser Cys Lys
            35                  40                  45

Asp Gly Lys Ala Ser Phe Thr Cys Thr Cys Lys Pro Gly Trp Gln Gly
    50                  55                  60

Glu Lys Cys Glu Phe Asp Ile Asn Glu Cys Lys Asp Pro Ser Asn Ile
65                  70                  75                  80

Asn Gly Gly Cys Ser Gln Ile Cys Asp Asn Thr Pro Gly Ser Tyr His
                85                  90                  95

Cys Ser Cys Lys Asn Gly Phe Val Met Leu Ser Asn Lys Lys Asp Cys
            100                 105                 110

Lys Asp Val Asp Glu Cys Ser Leu Lys Pro Ser Ile Cys Gly Thr Ala
        115                 120                 125

Val Cys Lys Asn Ile Pro Gly Asp Phe Glu Cys Glu Cys Pro Glu Gly
130                 135                 140

Tyr Arg Tyr Asn Leu Lys Ser Lys Ser Cys Glu Asp Ile Asp Glu Cys
145                 150                 155                 160

Ser Glu Asn Met Cys Ala Gln Leu Cys Val Asn Tyr Pro Gly Gly Tyr
                165                 170                 175

Thr Cys Tyr Cys Asp Gly Lys Lys Gly Phe Lys Leu Ala Gln Asp Gln
                180                 185                 190

Lys Ser Cys Glu
```

<210> SEQ ID NO 12
<211> LENGTH: 278
<212> TYPE: PRT
<213> ORGANISM: Artificial sequence
<220> FEATURE:
<223> OTHER INFORMATION: Synthetic

<400> SEQUENCE: 12

```
Met Ala Pro Ser Leu Ser Pro Gly Pro Ala Ala Leu Arg Arg Ala Pro
1               5                   10                  15

Gln Leu Leu Leu Leu Leu Ala Ala Glu Cys Ala Leu Ala Ala Leu
            20                  25                  30

Leu Pro Ala Arg Glu Ala Thr Gln Phe Leu Arg Pro Arg Gln Arg Arg
            35                  40                  45

Ala Phe Gln Val Phe Glu Glu Ala Lys Gln Gly His Leu Glu Arg Glu
        50                  55                  60

Cys Val Glu Glu Leu Cys Ser Arg Glu Ala Arg Glu Val Phe Glu
65                  70                  75                  80

Asn Asp Pro Glu Thr Asp Tyr Phe Tyr Pro Arg Tyr Leu Asp Cys Ile
                85                  90                  95

Asn Lys Tyr Gly Ser Pro Tyr Thr Lys Asn Ser Gly Phe Ala Thr Cys
            100                 105                 110

Val Gln Asn Leu Pro Asp Gln Cys Thr Pro Asn Pro Cys Asp Arg Lys
        115                 120                 125

Gly Thr Gln Ala Cys Gln Asp Leu Met Gly Asn Phe Phe Cys Leu Cys
    130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
        195                 200                 205

Glu Ala Arg Cys Lys Asn Leu Pro Gly Ser Tyr Ser Cys Leu Cys Asp
    210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu
        275
```

<210> SEQ ID NO 13
<211> LENGTH: 248
<212> TYPE: PRT
<213> ORGANISM: Artificial sequence
<220> FEATURE:
<223> OTHER INFORMATION: Synthetic

<400> SEQUENCE: 13

```
Ala Leu Leu Pro Ala Arg Glu Ala Thr Gln Phe Leu Arg Pro Arg Gln
1               5                   10                  15
```

```
Arg Arg Ala Phe Gln Val Phe Glu Glu Ala Lys Gln Gly His Leu Glu
            20                  25                  30

Arg Glu Cys Val Glu Glu Leu Cys Ser Arg Glu Glu Ala Arg Glu Val
        35                  40                  45

Phe Glu Asn Asp Pro Glu Thr Asp Tyr Phe Tyr Pro Arg Tyr Leu Asp
    50                  55                  60

Cys Ile Asn Lys Tyr Gly Ser Pro Tyr Thr Lys Asn Ser Gly Phe Ala
65                  70                  75                  80

Thr Cys Val Gln Asn Leu Pro Asp Gln Cys Thr Pro Asn Pro Cys Asp
                85                  90                  95

Arg Lys Gly Thr Gln Ala Cys Gln Asp Leu Met Gly Asn Phe Phe Cys
            100                 105                 110

Leu Cys Lys Ala Gly Trp Gly Gly Arg Leu Cys Asp Lys Asp Val Asn
        115                 120                 125

Glu Cys Ser Gln Glu Asn Gly Gly Cys Leu Gln Ile Cys His Asn Lys
    130                 135                 140

Pro Gly Ser Phe His Cys Ser Cys His Ser Gly Phe Glu Leu Ser Ser
145                 150                 155                 160

Asp Gly Arg Thr Cys Gln Asp Ile Asp Glu Cys Ala Asp Ser Glu Ala
                165                 170                 175

Cys Gly Glu Ala Arg Cys Lys Asn Leu Pro Gly Ser Tyr Ser Cys Leu
            180                 185                 190

Cys Asp Glu Gly Phe Ala Tyr Ser Ser Gln Glu Lys Ala Cys Arg Asp
        195                 200                 205

Val Asp Glu Cys Leu Gln Gly Arg Cys Glu Gln Val Cys Val Asn Ser
    210                 215                 220

Pro Gly Ser Tyr Thr Cys His Cys Asp Gly Arg Gly Gly Leu Lys Leu
225                 230                 235                 240

Ser Gln Asp Met Asp Thr Cys Glu
                245

<210> SEQ ID NO 14
<211> LENGTH: 230
<212> TYPE: PRT
<213> ORGANISM: Artificial sequence
<220> FEATURE:
<223> OTHER INFORMATION: Synthetic

<400> SEQUENCE: 14

Ala Phe Gln Val Phe Glu Glu Ala Lys Gln Gly His Leu Glu Arg Glu
1               5                   10                  15

Cys Val Glu Glu Leu Cys Ser Arg Glu Glu Ala Arg Glu Val Phe Glu
            20                  25                  30

Asn Asp Pro Glu Thr Asp Tyr Phe Tyr Pro Arg Tyr Leu Asp Cys Ile
        35                  40                  45

Asn Lys Tyr Gly Ser Pro Tyr Thr Lys Asn Ser Gly Phe Ala Thr Cys
    50                  55                  60

Val Gln Asn Leu Pro Asp Gln Cys Thr Pro Asn Pro Cys Asp Arg Lys
65                  70                  75                  80

Gly Thr Gln Ala Cys Gln Asp Leu Met Gly Asn Phe Phe Cys Leu Cys
                85                  90                  95

Lys Ala Gly Trp Gly Gly Arg Leu Cys Asp Lys Asp Val Asn Glu Cys
            100                 105                 110

Ser Gln Glu Asn Gly Gly Cys Leu Gln Ile Cys His Asn Lys Pro Gly
        115                 120                 125
```

```
Ser Phe His Cys Ser Cys His Ser Gly Phe Glu Leu Ser Ser Asp Gly
    130                 135                 140
Arg Thr Cys Gln Asp Ile Asp Glu Cys Ala Asp Ser Glu Ala Cys Gly
145                 150                 155                 160
Glu Ala Arg Cys Lys Asn Leu Pro Gly Ser Tyr Ser Cys Leu Cys Asp
                165                 170                 175
Glu Gly Phe Ala Tyr Ser Ser Gln Glu Lys Ala Cys Arg Asp Val Asp
            180                 185                 190
Glu Cys Leu Gln Gly Arg Cys Glu Gln Val Cys Val Asn Ser Pro Gly
        195                 200                 205
Ser Tyr Thr Cys His Cys Asp Gly Arg Gly Leu Lys Leu Ser Gln
    210                 215                 220
Asp Met Asp Thr Cys Glu
225                 230

<210> SEQ ID NO 15
<211> LENGTH: 283
<212> TYPE: PRT
<213> ORGANISM: Artificial sequence
<220> FEATURE:
<223> OTHER INFORMATION: Synthetic

<400> SEQUENCE: 15

Met Arg Val Leu Gly Gly Arg Cys Gly Ala Leu Leu Ala Cys Leu Leu
1               5                   10                  15
Leu Val Leu Pro Val Ser Glu Ala Asn Phe Leu Ser Lys Gln Gln Ala
            20                  25                  30
Ser Gln Val Leu Val Arg Lys Arg Arg Ala Asn Ser Leu Leu Glu Glu
        35                  40                  45
Thr Lys Gln Gly Asn Leu Glu Arg Glu Cys Ile Glu Glu Leu Cys Asn
    50                  55                  60
Lys Glu Glu Ala Arg Glu Val Phe Glu Asn Asp Pro Glu Thr Asp Tyr
65                  70                  75                  80
Phe Tyr Pro Lys Tyr Leu Val Cys Leu Arg Ser Phe Gln Thr Gly Leu
                85                  90                  95
Phe Thr Ala Ala Arg Gln Ser Thr Asn Ala Tyr Pro Asp Leu Arg Ser
            100                 105                 110
Cys Val Asn Ala Ile Pro Asp Gln Cys Ser Pro Leu Pro Cys Asn Glu
        115                 120                 125
Asp Gly Tyr Met Ser Cys Lys Asp Gly Lys Ala Ser Phe Thr Cys Thr
    130                 135                 140
Cys Lys Pro Gly Trp Gln Gly Glu Lys Cys Glu Phe Asp Ile Asn Glu
145                 150                 155                 160
Cys Lys Asp Pro Ser Asn Ile Asn Gly Gly Cys Ser Gln Ile Cys Asp
                165                 170                 175
Asn Thr Pro Gly Ser Tyr His Cys Ser Cys Lys Asn Gly Phe Val Met
            180                 185                 190
Leu Ser Asn Lys Lys Asp Cys Lys Asp Val Asp Glu Cys Ser Leu Lys
        195                 200                 205
Pro Ser Ile Cys Gly Thr Ala Val Cys Lys Asn Ile Pro Gly Asp Phe
    210                 215                 220
Glu Cys Glu Cys Pro Glu Gly Tyr Arg Tyr Asn Leu Lys Ser Lys Ser
225                 230                 235                 240
Cys Glu Asp Ile Asp Glu Cys Ser Glu Asn Met Cys Ala Gln Leu Cys
                245                 250                 255
```

Val Asn Tyr Pro Gly Gly Tyr Thr Cys Tyr Cys Asp Gly Lys Lys Gly
            260                 265                 270

Phe Lys Leu Ala Gln Asp Gln Lys Ser Cys Glu
        275                 280

<210> SEQ ID NO 16
<211> LENGTH: 259
<212> TYPE: PRT
<213> ORGANISM: Artificial sequence
<220> FEATURE:
<223> OTHER INFORMATION: Synthetic

<400> SEQUENCE: 16

Asn Phe Leu Ser Lys Gln Gln Ala Ser Gln Val Leu Val Arg Lys Arg
1               5                   10                  15

Arg Ala Asn Ser Leu Leu Glu Glu Thr Lys Gln Gly Asn Leu Glu Arg
            20                  25                  30

Glu Cys Ile Glu Glu Leu Cys Asn Lys Glu Glu Ala Arg Glu Val Phe
        35                  40                  45

Glu Asn Asp Pro Glu Thr Asp Tyr Phe Tyr Pro Lys Tyr Leu Val Cys
    50                  55                  60

Leu Arg Ser Phe Gln Thr Gly Leu Phe Thr Ala Ala Arg Gln Ser Thr
65                  70                  75                  80

Asn Ala Tyr Pro Asp Leu Arg Ser Cys Val Asn Ala Ile Pro Asp Gln
                85                  90                  95

Cys Ser Pro Leu Pro Cys Asn Glu Asp Gly Tyr Met Ser Cys Lys Asp
            100                 105                 110

Gly Lys Ala Ser Phe Thr Cys Thr Cys Lys Pro Gly Trp Gln Gly Glu
        115                 120                 125

Lys Cys Glu Phe Asp Ile Asn Glu Cys Lys Asp Pro Ser Asn Ile Asn
    130                 135                 140

Gly Gly Cys Ser Gln Ile Cys Asp Asn Thr Pro Gly Ser Tyr His Cys
145                 150                 155                 160

Ser Cys Lys Asn Gly Phe Val Met Leu Ser Asn Lys Lys Asp Cys Lys
                165                 170                 175

Asp Val Asp Glu Cys Ser Leu Lys Pro Ser Ile Cys Gly Thr Ala Val
            180                 185                 190

Cys Lys Asn Ile Pro Gly Asp Phe Glu Cys Glu Cys Pro Glu Gly Tyr
        195                 200                 205

Arg Tyr Asn Leu Lys Ser Lys Ser Cys Glu Asp Ile Asp Glu Cys Ser
    210                 215                 220

Glu Asn Met Cys Ala Gln Leu Cys Val Asn Tyr Pro Gly Gly Tyr Thr
225                 230                 235                 240

Cys Tyr Cys Asp Gly Lys Lys Gly Phe Lys Leu Ala Gln Asp Gln Lys
                245                 250                 255

Ser Cys Glu

<210> SEQ ID NO 17
<211> LENGTH: 242
<212> TYPE: PRT
<213> ORGANISM: Artificial sequence
<220> FEATURE:
<223> OTHER INFORMATION: Synthetic

<400> SEQUENCE: 17

Ala Asn Ser Leu Leu Glu Glu Thr Lys Gln Gly Asn Leu Glu Arg Glu
1               5                   10                  15

Cys Ile Glu Glu Leu Cys Asn Lys Glu Ala Arg Glu Val Phe Glu
                20                  25                  30

Asn Asp Pro Glu Thr Asp Tyr Phe Tyr Pro Lys Tyr Leu Val Cys Leu
            35                  40                  45

Arg Ser Phe Gln Thr Gly Leu Phe Thr Ala Ala Arg Gln Ser Thr Asn
50                  55                  60

Ala Tyr Pro Asp Leu Arg Ser Cys Val Asn Ala Ile Pro Asp Gln Cys
65                  70                  75                  80

Ser Pro Leu Pro Cys Asn Glu Asp Gly Tyr Met Ser Cys Lys Asp Gly
                85                  90                  95

Lys Ala Ser Phe Thr Cys Thr Cys Lys Pro Gly Trp Gln Gly Glu Lys
                100                 105                 110

Cys Glu Phe Asp Ile Asn Glu Cys Lys Asp Pro Ser Asn Ile Asn Gly
            115                 120                 125

Gly Cys Ser Gln Ile Cys Asp Asn Thr Pro Gly Ser Tyr His Cys Ser
            130                 135                 140

Cys Lys Asn Gly Phe Val Met Leu Ser Asn Lys Lys Asp Cys Lys Asp
145                 150                 155                 160

Val Asp Glu Cys Ser Leu Lys Pro Ser Ile Cys Gly Thr Ala Val Cys
                165                 170                 175

Lys Asn Ile Pro Gly Asp Phe Glu Cys Glu Cys Pro Glu Gly Tyr Arg
            180                 185                 190

Tyr Asn Leu Lys Ser Lys Ser Cys Glu Asp Ile Asp Glu Cys Ser Glu
            195                 200                 205

Asn Met Cys Ala Gln Leu Cys Val Asn Tyr Pro Gly Gly Tyr Thr Cys
210                 215                 220

Tyr Cys Asp Gly Lys Lys Gly Phe Lys Leu Ala Gln Asp Gln Lys Ser
225                 230                 235                 240

Cys Glu

<210> SEQ ID NO 18
<211> LENGTH: 173
<212> TYPE: PRT
<213> ORGANISM: Homo sapien

<400> SEQUENCE: 18

Cys Lys Ser Ser Cys Ser Val Gly Cys Asp Leu Pro Gln Thr His Ser
1               5                   10                  15

Leu Gly Ser Arg Arg Thr Leu Met Leu Leu Ala Gln Met Arg Arg Ile
                20                  25                  30

Ser Leu Phe Ser Cys Leu Lys Asp Arg His Asp Phe Gly Phe Pro Gln
            35                  40                  45

Glu Glu Phe Gly Asn Gln Phe Gln Lys Ala Glu Thr Ile Pro Val Leu
50                  55                  60

His Glu Met Ile Gln Gln Ile Phe Asn Leu Phe Ser Thr Lys Asp Ser
65                  70                  75                  80

Ser Ala Ala Trp Asp Glu Thr Leu Leu Asp Lys Phe Tyr Thr Glu Leu
                85                  90                  95

Tyr Gln Gln Leu Asn Asp Leu Glu Ala Cys Val Ile Gln Gly Val Gly
            100                 105                 110

Val Thr Glu Thr Pro Leu Met Lys Glu Asp Ser Ile Leu Ala Val Arg
            115                 120                 125

Lys Tyr Phe Gln Arg Ile Thr Leu Tyr Leu Lys Glu Lys Lys Tyr Ser
130                 135                 140

```
Pro Cys Ala Trp Glu Val Val Arg Ala Glu Ile Met Arg Ser Phe Ser
145                 150                 155                 160

Leu Ser Thr Asn Leu Gln Glu Ser Leu Arg Ser Lys Glu
                165                 170
```

<210> SEQ ID NO 19
<211> LENGTH: 166
<212> TYPE: PRT
<213> ORGANISM: Homo sapien

<400> SEQUENCE: 19

```
Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
                35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
                115                 120                 125

Ile Leu His Tyr Leu Lys Ala Lys Glu Tyr Ser His Cys Ala Trp Thr
        130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

<210> SEQ ID NO 20
<211> LENGTH: 180
<212> TYPE: PRT
<213> ORGANISM: Homo sapien

<400> SEQUENCE: 20

```
Pro Val Pro Thr Ser Lys Pro Thr Pro Thr Gly Lys Gly Cys His Ile
1               5                   10                  15

Gly Arg Phe Lys Ser Leu Ser Pro Gln Glu Leu Ala Ser Phe Lys Lys
                20                  25                  30

Ala Arg Asp Ala Leu Glu Glu Ser Leu Lys Leu Lys Asn Trp Ser Cys
                35                  40                  45

Ser Ser Pro Val Phe Pro Gly Asn Trp Asp Leu Arg Leu Leu Gln Val
        50                  55                  60

Arg Glu Arg Pro Val Ala Leu Glu Ala Glu Leu Ala Leu Thr Leu Lys
65                  70                  75                  80

Val Leu Glu Ala Ala Ala Gly Pro Ala Leu Glu Asp Val Leu Asp Gln
                85                  90                  95

Pro Leu His Thr Leu His His Ile Leu Ser Gln Leu Gln Ala Cys Ile
                100                 105                 110

Gln Pro Gln Pro Thr Ala Gly Pro Arg Pro Arg Gly Arg Leu His His
        115                 120                 125
```

```
Trp Leu His Arg Leu Gln Glu Ala Pro Lys Lys Glu Ser Ala Gly Cys
            130                 135                 140
Leu Glu Ala Ser Val Thr Phe Asn Leu Phe Arg Leu Leu Thr Arg Asp
145                 150                 155                 160
Leu Lys Tyr Val Ala Asp Gly Asn Leu Cys Leu Arg Thr Ser Thr His
                165                 170                 175
Pro Glu Ser Thr
            180

<210> SEQ ID NO 21
<211> LENGTH: 175
<212> TYPE: PRT
<213> ORGANISM: Homo sapien

<400> SEQUENCE: 21

Val Pro Val Ala Arg Leu Arg Gly Ala Leu Pro Asp Ala Arg Gly Cys
1               5                   10                  15
His Ile Ala Gln Phe Lys Ser Leu Ser Pro Gln Glu Leu Gln Ala Phe
                20                  25                  30
Lys Arg Ala Lys Asp Ala Leu Glu Glu Ser Leu Leu Leu Lys Asp Cys
            35                  40                  45
Lys Cys Arg Ser Arg Leu Phe Pro Arg Thr Trp Asp Leu Arg Gln Leu
        50                  55                  60
Gln Val Arg Glu Arg Pro Val Ala Leu Glu Ala Glu Leu Ala Leu Thr
65                  70                  75                  80
Leu Lys Val Leu Glu Ala Ser Ala Asp Thr Asp Pro Ala Leu Gly Asp
                85                  90                  95
Val Leu Asp Gln Pro Leu His Thr Leu His His Ile Leu Ser Gln Leu
                100                 105                 110
Arg Ala Cys Ile Gln Pro Gln Pro Thr Ala Gly Pro Arg Thr Arg Gly
            115                 120                 125
Arg Leu His His Trp Leu Tyr Arg Leu Gln Glu Ala Pro Lys Lys Glu
        130                 135                 140
Ser Pro Gly Cys Leu Glu Ala Ser Val Thr Phe Asn Leu Phe Arg Leu
145                 150                 155                 160
Leu Thr Arg Asp Leu Asn Cys Val Ala Ser Gly Asp Leu Cys Val
                165                 170                 175

<210> SEQ ID NO 22
<211> LENGTH: 11
<212> TYPE: PRT
<213> ORGANISM: Artificial sequence
<220> FEATURE:
<223> OTHER INFORMATION: Synthetic

<400> SEQUENCE: 22

Gly Ser Ser Gly Ser Ser Gly Ser Ser Gly Ser
1               5                   10

<210> SEQ ID NO 23
<211> LENGTH: 12
<212> TYPE: PRT
<213> ORGANISM: Artificial sequence
<220> FEATURE:
<223> OTHER INFORMATION: Synthetic

<400> SEQUENCE: 23

Gly Ser Asn Gly Gly Phe Asp Ser Ser Glu Gly Gly
1               5                   10
```

```
<210> SEQ ID NO 24
<211> LENGTH: 10
<212> TYPE: PRT
<213> ORGANISM: Artificial sequence
<220> FEATURE:
<223> OTHER INFORMATION: Synthetic

<400> SEQUENCE: 24

Ser Ser Gly Ser Ser Gly Ser Ser Gly Ser
1               5                   10

<210> SEQ ID NO 25
<211> LENGTH: 12
<212> TYPE: PRT
<213> ORGANISM: Artificial sequence
<220> FEATURE:
<223> OTHER INFORMATION: Synthetic

<400> SEQUENCE: 25

Gly Ser Ser Gly Gly Ser Gly Gly Ser Gly Gly Gly
1               5                   10

<210> SEQ ID NO 26
<211> LENGTH: 12
<212> TYPE: PRT
<213> ORGANISM: Artificial sequence
<220> FEATURE:
<223> OTHER INFORMATION: Synthetic

<400> SEQUENCE: 26

Gly Ser Ser Ser Asp Ser Asp Ser Ser Ala Gly Ser
1               5                   10

<210> SEQ ID NO 27
<211> LENGTH: 12
<212> TYPE: PRT
<213> ORGANISM: Artificial sequence
<220> FEATURE:
<223> OTHER INFORMATION: Synthetic

<400> SEQUENCE: 27

Gly Ser Asn Asp Ser Ser Gly Gly Ser Glu Gly Gly
1               5                   10

<210> SEQ ID NO 28
<211> LENGTH: 12
<212> TYPE: PRT
<213> ORGANISM: Artificial sequence
<220> FEATURE:
<223> OTHER INFORMATION: Synthetic

<400> SEQUENCE: 28

Gly Ser Ile Arg Trp Ser Gly Leu Ser Gly Gly Asp
1               5                   10

<210> SEQ ID NO 29
<211> LENGTH: 12
<212> TYPE: PRT
<213> ORGANISM: Artificial sequence
<220> FEATURE:
<223> OTHER INFORMATION: Synthetic

<400> SEQUENCE: 29

Gly Ser Arg Gly Gly Ser Val Tyr Ser Glu Gly Gly
1               5                   10
```

```
<210> SEQ ID NO 30
<211> LENGTH: 12
<212> TYPE: PRT
<213> ORGANISM: Artificial sequence
<220> FEATURE:
<223> OTHER INFORMATION: Synthetic

<400> SEQUENCE: 30

Gly Ser Ser Glu Gly Ser Ser Asp Phe Gly Gly Asp
1               5                   10

<210> SEQ ID NO 31
<211> LENGTH: 12
<212> TYPE: PRT
<213> ORGANISM: Artificial sequence
<220> FEATURE:
<223> OTHER INFORMATION: Synthetic

<400> SEQUENCE: 31

Gly Ser Ile Val Val Ser Cys Ser Ser Glu Gly Gly
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic

<400> SEQUENCE: 32

Gly Ser Asn Trp Asp Ser Gly Cys Ser Arg Glu Gly
1               5                   10

<210> SEQ ID NO 33
<211> LENGTH: 12
<212> TYPE: PRT
<213> ORGANISM: Artificial sequence
<220> FEATURE:
<223> OTHER INFORMATION: Synthetic

<400> SEQUENCE: 33

Gly Ser Asn Trp Asp Ser Gly Cys Ser Arg Glu Cys
1               5                   10

<210> SEQ ID NO 34
<211> LENGTH: 12
<212> TYPE: PRT
<213> ORGANISM: Artificial sequence
<220> FEATURE:
<223> OTHER INFORMATION: Synthetic

<400> SEQUENCE: 34

Gly Ser Ser Gly Cys Thr Gly Asp Ala Gly Gly Ser
1               5                   10

<210> SEQ ID NO 35
<211> LENGTH: 12
<212> TYPE: PRT
<213> ORGANISM: Artificial sequence
<220> FEATURE:
<223> OTHER INFORMATION: Synthetic

<400> SEQUENCE: 35

Gly Ser Asn Trp Asp Ser Gly Cys Ser Arg Gln Cys
1               5                   10

<210> SEQ ID NO 36
```

```
<211> LENGTH: 12
<212> TYPE: PRT
<213> ORGANISM: Artificial sequence
<220> FEATURE:
<223> OTHER INFORMATION: Synthetic

<400> SEQUENCE: 36

Gly Ser Ile Ala Gly Cys Gly Asp Ala Gly Glu Gly
1               5                   10

<210> SEQ ID NO 37
<211> LENGTH: 11
<212> TYPE: PRT
<213> ORGANISM: Artificial sequence
<220> FEATURE:
<223> OTHER INFORMATION: Synthetic

<400> SEQUENCE: 37

Gly Ser Asn Trp Asp Ser Gly Cys Ser Arg Glu
1               5                   10

<210> SEQ ID NO 38
<211> LENGTH: 12
<212> TYPE: PRT
<213> ORGANISM: Artificial sequence
<220> FEATURE:
<223> OTHER INFORMATION: Synthetic

<400> SEQUENCE: 38

Gly Ser Asn Trp Asp Ser Gly Cys Ser Arg Glu Gly
1               5                   10

<210> SEQ ID NO 39
<211> LENGTH: 10
<212> TYPE: PRT
<213> ORGANISM: Artificial sequence
<220> FEATURE:
<223> OTHER INFORMATION: Synthetic

<400> SEQUENCE: 39

Asn Trp Asp Ser Gly Cys Ser Arg Glu Gly
1               5                   10

<210> SEQ ID NO 40
<211> LENGTH: 10
<212> TYPE: PRT
<213> ORGANISM: Artificial sequence
<220> FEATURE:
<223> OTHER INFORMATION: Synthetic

<400> SEQUENCE: 40

Ile Ala Gly Cys Gly Asp Ala Gly Glu Gly
1               5                   10

<210> SEQ ID NO 41
<211> LENGTH: 28
<212> TYPE: PRT
<213> ORGANISM: Artificial sequence
<220> FEATURE:
<223> OTHER INFORMATION: Synthetic

<400> SEQUENCE: 41

Ser Arg Arg Ala Ser Gly Ser Gly Gly Ser Ser Gly Thr Ser Gly
1               5                   10                  15

Ser Ser Gly Gly Ser Ser Gly Thr Ser Thr Asp Pro
            20                  25
```

<210> SEQ ID NO 42
<211> LENGTH: 22
<212> TYPE: PRT
<213> ORGANISM: Artificial sequence
<220> FEATURE:
<223> OTHER INFORMATION: Synthetic

<400> SEQUENCE: 42

Ala Ser Gly Ser Ser Gly Gly Ser Ser Gly Thr Ser Gly Ser Ser Gly
1               5                   10                  15

Gly Ser Ser Gly Thr Ser
            20

<210> SEQ ID NO 43
<211> LENGTH: 25
<212> TYPE: PRT
<213> ORGANISM: Artificial sequence
<220> FEATURE:
<223> OTHER INFORMATION: Synthetic

<400> SEQUENCE: 43

Ala Ser Gly Ser Ser Gly Gly Ser Ser Gly Thr Ser Gly Ser Ser Gly
1               5                   10                  15

Gly Ser Ser Gly Thr Ser Thr Asp Pro
            20                  25

<210> SEQ ID NO 44
<211> LENGTH: 5
<212> TYPE: PRT
<213> ORGANISM: Artificial sequence
<220> FEATURE:
<223> OTHER INFORMATION: Synthetic

<400> SEQUENCE: 44

Gly Gly Gly Gly Ser
1               5

<210> SEQ ID NO 45
<211> LENGTH: 10
<212> TYPE: PRT
<213> ORGANISM: Artificial sequence
<220> FEATURE:
<223> OTHER INFORMATION: Synthetic

<400> SEQUENCE: 45

Gly Gly Gly Gly Ser Gly Gly Gly Gly Ser
1               5                   10

<210> SEQ ID NO 46
<211> LENGTH: 14
<212> TYPE: PRT
<213> ORGANISM: Artificial sequence
<220> FEATURE:
<223> OTHER INFORMATION: Synthetic

<400> SEQUENCE: 46

Gly Gly Gly Gly Ser Gly Gly Gly Ser Gly Gly Gly Gly Ser
1               5                   10

<210> SEQ ID NO 47
<211> LENGTH: 22
<212> TYPE: PRT
<213> ORGANISM: Artificial sequence
<220> FEATURE:
<223> OTHER INFORMATION: Synthetic -continued

<400> SEQUENCE: 47

Gly Ser Ser Gly Ser Ser Gly Ser Ser Gly Ser Ser Gly Ser Ser Gly Ser
1               5                   10                  15

Ser Gly Ser Ser Gly Ser
            20

<210> SEQ ID NO 48
<211> LENGTH: 12
<212> TYPE: PRT
<213> ORGANISM: Artificial sequence
<220> FEATURE:
<223> OTHER INFORMATION: Synthetic

<400> SEQUENCE: 48

Ala Ser Gly Ser Ser Gly Gly Ser Ser Gly Thr Ser
1               5                   10

<210> SEQ ID NO 49
<211> LENGTH: 653
<212> TYPE: PRT
<213> ORGANISM: Artificial sequence
<220> FEATURE:
<223> OTHER INFORMATION: Synthetic

<400> SEQUENCE: 49

Met Pro Pro Pro Gly Pro Ala Ala Ala Leu Gly Thr Ala Leu Leu
1               5                   10                  15

Leu Leu Leu Leu Ala Ser Glu Ser Ser His Thr Val Leu Leu Arg Ala
                20                  25                  30

Arg Glu Ala Ala Gln Phe Leu Arg Pro Arg Gln Arg Ala Tyr Gln
                35                  40                  45

Val Phe Glu Glu Ala Lys Gln Gly His Leu Glu Arg Glu Cys Val Glu
    50                  55                  60

Glu Val Cys Ser Lys Glu Ala Arg Glu Val Phe Glu Asn Asp Pro Glu
65                  70                  75                  80

Thr Glu Tyr Phe Tyr Pro Arg Tyr Gln Glu Cys Met Arg Lys Tyr Gly
                    85                  90                  95

Arg Pro Glu Glu Lys Asn Pro Asp Phe Ala Lys Cys Val Gln Asn Leu
                100                 105                 110

Pro Asp Gln Cys Thr Pro Asn Pro Cys Asp Lys Lys Gly Thr His Ile
            115                 120                 125

Cys Gln Asp Leu Met Gly Asn Phe Phe Cys Val Cys Thr Asp Gly Trp
    130                 135                 140

Gly Gly Arg Leu Cys Asp Lys Asp Val Asn Glu Cys Val Gln Lys Asn
145                 150                 155                 160

Gly Gly Cys Ser Gln Val Cys His Asn Lys Pro Gly Ser Phe Gln Cys
                165                 170                 175

Ala Cys His Ser Gly Phe Ser Leu Ala Ser Asp Gly Gln Thr Cys Gln
                180                 185                 190

Asp Ile Asp Glu Cys Thr Asp Ser Asp Thr Cys Gly Asp Ala Arg Cys
            195                 200                 205

Lys Leu Pro Gly Ser Tyr Ser Cys Leu Cys Asp Glu Gly Tyr Thr Tyr
    210                 215                 220

Ser Ser Lys Glu Lys Thr Cys Gln Asp Val Asp Glu Cys Gln Gln Asp
225                 230                 235                 240

Arg Cys Glu Gln Thr Cys Val Asn Ser Pro Gly Ser Tyr Thr Cys His
                245                 250                 255

```
Cys Asp Gly Arg Gly Leu Lys Leu Ser Pro Asp Met Asp Thr Cys
            260                 265                 270

Glu Ala Ser Gly Ser Ser Gly Ser Ser Gly Thr Ser Gly Ser Ser
        275                 280                 285

Gly Gly Ser Ser Gly Thr Ser Ile Asn Tyr Arg Gln Leu Gln Leu Gln
        290                 295                 300

Glu Arg Thr Asn Ile Arg Lys Ser Gln Glu Leu Leu Glu Gln Leu Asn
305                 310                 315                 320

Gly Lys Ile Asn Leu Thr Tyr Arg Ala Asp Phe Lys Ile Pro Met Glu
                325                 330                 335

Met Thr Glu Lys Met Gln Lys Ser Tyr Thr Ala Phe Ala Ile Gln Glu
            340                 345                 350

Met Leu Gln Asn Val Phe Leu Val Phe Arg Asn Asn Phe Ser Ser Thr
        355                 360                 365

Gly Trp Asn Glu Thr Ile Val Val Arg Leu Leu Asp Glu Leu His Gln
        370                 375                 380

Gln Thr Val Phe Leu Lys Thr Val Leu Glu Glu Lys Glu Glu Arg
385                 390                 395                 400

Leu Thr Trp Glu Met Ser Ser Thr Ala Leu His Leu Lys Ser Tyr Tyr
                405                 410                 415

Trp Arg Val Gln Arg Tyr Leu Lys Leu Met Lys Tyr Asn Ser Tyr Ala
            420                 425                 430

Trp Met Val Val Arg Ala Glu Ile Phe Arg Asn Phe Leu Ile Ile Arg
        435                 440                 445

Arg Leu Thr Arg Asn Phe Gln Asn Ala Ser Gly Ser Ser Gly Gly Ser
        450                 455                 460

Ser Gly Thr Ser Gly Ser Ser Gly Gly Ser Ser Gly Thr Ser Thr Asp
465                 470                 475                 480

Pro Val Pro Arg Ala Thr Arg Leu Pro Val Glu Ala Lys Asp Cys His
                485                 490                 495

Ile Ala Gln Phe Lys Ser Leu Ser Pro Lys Glu Leu Gln Ala Phe Lys
            500                 505                 510

Lys Ala Lys Asp Ala Ile Glu Lys Arg Leu Leu Glu Lys Asp Met Arg
        515                 520                 525

Cys Ser Ser His Leu Ile Ser Arg Ala Trp Asp Leu Lys Gln Leu Gln
        530                 535                 540

Val Gln Glu Arg Pro Lys Ala Leu Gln Ala Glu Val Ala Leu Thr Leu
545                 550                 555                 560

Lys Val Trp Glu Asn Met Thr Asp Ser Ala Leu Ala Thr Ile Leu Gly
                565                 570                 575

Gln Pro Leu His Thr Leu Ser His Ile His Ser Gln Leu Gln Thr Cys
            580                 585                 590

Thr Gln Leu Gln Ala Thr Ala Glu Pro Lys Pro Ser Arg Arg Leu
        595                 600                 605

Ser Arg Trp Leu His Arg Leu Gln Glu Ala Gln Ser Lys Glu Thr Pro
        610                 615                 620

Gly Cys Leu Glu Asp Ser Val Thr Ser Asn Leu Phe Arg Leu Leu Thr
625                 630                 635                 640

Arg Asp Leu Lys Cys Val Ala Ser Gly Asp Gln Cys Val
                645                 650

<210> SEQ ID NO 50
<211> LENGTH: 664
<212> TYPE: PRT
```

<213> ORGANISM: Artificial sequence
<220> FEATURE:
<223> OTHER INFORMATION: Synthetic

<400> SEQUENCE: 50

```
Met Ala Pro Ser Leu Ser Pro Gly Pro Ala Ala Leu Arg Arg Ala Pro
1               5                   10                  15

Gln Leu Leu Leu Leu Leu Ala Ala Glu Cys Ala Leu Ala Ala Leu
            20                  25                  30

Leu Pro Ala Arg Glu Ala Thr Gln Phe Leu Arg Pro Gln Arg Arg
        35                  40                  45

Ala Phe Gln Val Phe Glu Glu Ala Lys Gln Gly His Leu Glu Arg Glu
    50                  55                  60

Cys Val Glu Glu Leu Cys Ser Arg Glu Glu Ala Arg Glu Val Phe Glu
65                  70                  75                  80

Asn Asp Pro Glu Thr Asp Tyr Phe Tyr Pro Arg Tyr Leu Asp Cys Ile
                85                  90                  95

Asn Lys Tyr Gly Ser Pro Tyr Thr Lys Asn Ser Gly Phe Ala Thr Cys
            100                 105                 110

Val Gln Asn Leu Pro Asp Gln Cys Thr Pro Asn Pro Cys Asp Arg Lys
        115                 120                 125

Gly Thr Gln Ala Cys Gln Asp Leu Met Gly Asn Phe Phe Cys Leu Cys
    130                 135                 140

Lys Ala Gly Trp Gly Gly Arg Leu Cys Asp Lys Asp Val Asn Glu Cys
145                 150                 155                 160

Ser Gln Glu Asn Gly Gly Cys Leu Gln Ile Cys His Asn Lys Pro Gly
                165                 170                 175

Ser Phe His Cys Ser Cys His Ser Gly Phe Glu Leu Ser Ser Asp Gly
            180                 185                 190

Arg Thr Cys Gln Asp Ile Asp Glu Cys Ala Asp Ser Glu Ala Cys Gly
        195                 200                 205

Glu Ala Arg Cys Lys Asn Leu Pro Gly Ser Tyr Ser Cys Leu Cys Asp
    210                 215                 220

Glu Gly Phe Ala Tyr Ser Ser Gln Glu Lys Ala Cys Arg Asp Val Asp
225                 230                 235                 240

Glu Cys Leu Gln Gly Arg Cys Glu Gln Val Cys Val Asn Ser Pro Gly
                245                 250                 255

Ser Tyr Thr Cys His Cys Asp Gly Arg Gly Gly Leu Lys Leu Ser Gln
            260                 265                 270

Asp Met Asp Thr Cys Glu Ala Ser Gly Ser Ser Gly Ser Ser Gly
        275                 280                 285

Thr Ser Gly Ser Ser Gly Gly Ser Ser Gly Thr Ser Met Ser Tyr Asn
    290                 295                 300

Leu Leu Gly Phe Leu Gln Arg Ser Ser Asn Phe Gln Cys Gln Lys Leu
305                 310                 315                 320

Leu Trp Gln Leu Asn Gly Arg Leu Glu Tyr Cys Leu Lys Asp Arg Met
                325                 330                 335

Asn Phe Asp Ile Pro Glu Glu Ile Lys Gln Leu Gln Gln Phe Gln Lys
            340                 345                 350

Glu Asp Ala Ala Leu Thr Ile Tyr Glu Met Leu Gln Asn Ile Phe Ala
        355                 360                 365

Ile Phe Arg Gln Asp Ser Ser Ser Thr Gly Trp Asn Glu Thr Ile Val
    370                 375                 380

Glu Asn Leu Leu Ala Asn Val Tyr His Gln Ile Asn His Leu Lys Thr
```

-continued

```
            385                 390                 395                 400
Val Leu Glu Glu Lys Leu Glu Lys Glu Asp Phe Thr Arg Gly Lys Leu
                    405                 410                 415

Met Ser Ser Leu His Leu Lys Arg Tyr Tyr Gly Arg Ile Leu His Tyr
                420                 425                 430

Leu Lys Ala Lys Glu Tyr Ser His Cys Ala Trp Thr Ile Val Arg Val
            435                 440                 445

Glu Ile Leu Arg Asn Phe Tyr Phe Ile Asn Arg Leu Thr Gly Tyr Leu
        450                 455                 460

Arg Asn Ala Ser Gly Ser Ser Gly Ser Ser Gly Thr Ser Gly Ser
465                 470                 475                 480

Ser Gly Gly Ser Ser Gly Thr Ser Thr Asp Pro Val Ala Arg Leu Arg
                485                 490                 495

Gly Ala Leu Pro Asp Ala Arg Gly Cys His Ile Ala Gln Phe Lys Ser
                500                 505                 510

Leu Ser Pro Gln Glu Leu Gln Ala Phe Lys Arg Ala Lys Asp Ala Leu
                515                 520                 525

Glu Glu Ser Leu Leu Leu Lys Asp Cys Lys Cys Arg Ser Arg Leu Phe
            530                 535                 540

Pro Arg Thr Trp Asp Leu Arg Gln Leu Gln Val Arg Glu Arg Pro Val
545                 550                 555                 560

Ala Leu Glu Ala Glu Leu Ala Leu Thr Leu Lys Val Leu Glu Ala Ser
                565                 570                 575

Ala Asp Thr Asp Pro Ala Leu Gly Asp Val Leu Asp Gln Pro Leu His
                580                 585                 590

Thr Leu His His Ile Leu Ser Gln Leu Arg Ala Cys Ile Gln Pro Gln
            595                 600                 605

Pro Thr Ala Gly Pro Arg Thr Arg Gly Arg Leu His His Trp Leu Tyr
            610                 615                 620

Arg Leu Gln Glu Ala Pro Lys Lys Glu Ser Pro Gly Cys Leu Glu Ala
625                 630                 635                 640

Ser Val Thr Phe Asn Leu Phe Arg Leu Leu Thr Arg Asp Leu Asn Cys
                645                 650                 655

Val Ala Ser Gly Asp Leu Cys Val
                660
```

PHOSPHATIDYLSERINE TARGETING FUSION MOLECULES AND METHODS FOR THEIR USE

This patent application is the National Stage of International Application No. PCT/US2018/043357 filed Jul. 24, 2018, which claims the benefit of priority from U.S. Provisional Application Ser. No. 62/536,107 filed Jul. 24, 2017, the content of each of which is herein incorporated by reference in its entirety.

FIELD

The present invention relates to fusion molecules comprising a cytokine and a polypeptide which targets the fusion molecule to phosphatidylserine (PS), pharmaceutical compositions comprising these fusion molecules, and methods for use of these fusion molecules in targeting a cytokine to a pathological site and treating a disease or condition responsive to cytokine treatment.

BACKGROUND

Phosphatidylserine (PS), an anionic phospholipid externalized on the surface of apoptotic cells, apoptotic blebs, exosomes, stressed tumor cells and the tumor vasculature is an immunosuppressive molecule in the tumor microenvironment (Birge et al. Cell Death and Differentiation 2016 23:962-978). Due to hypoxia and other metabolic stress, high apoptotic indexes of apoptotic cells, and release of tumor derived exosomes, up-regulation of PS in the tumor microenvironment has been observed in virtually all solid cancers (He et al. Clin. Cancer Res. 2009 15: 6871-6880). The up-regulated PS in turn interacts with the overexpressed Tyro3, Axl and Mer (TAM) receptors on the tumor cells and on the infiltrating myeloid-derived phagocytes. Collectively, PS/PS receptor engagement induces PS-dependent efferocytosis and the production of immunosuppressive cytokines such as IL-10 and TGF-β (Huynh et al. J. Clin. Invest. 2002 109:41-50; Rothlin et al. Cell 2007 131: 1124-1136).

In addition to tumor microenvironment, PS is also externalized by infected cells, particularly virus infected cells (Soares et al. Nat. Med. 2008 207:763-776; Dowall et al. J. Immunol. Res. 2015 347903). Moreover, a diverse variety of enveloped viruses expose PS on their surface and use it to not only suppress immune response and promote tolerance against viral antigens, but also utilize TAM receptors as a mechanism for virus entry into the cells (Birge et al. Cell Death. Differ. 2016 23:962-978). Growth arrest-specific gene 6 (GAS6) and protein S (Pros1) opsonized virus particles have been shown to interact with TAMs, become efferocytosed, uncoated in the endosomes and enter the cytoplasm.

However, while PS is constitutively elevated in the tumor microenvironment and on the surface of enveloped viruses, under normal physiological conditions un-cleared apoptotic cells are rarely observed, even in tissues with high rates of cellular turnover such as the thymus and spleen. Thus, PS is not detected in healthy tissues (Gerber et al. Clin. Cancer Res. 2011 17:6888-6896).

Therefore, PS-targeting has been disclosed as a possible means for localized delivery of a therapeutic agent to sites with pathologies where PS is up-regulated as a part of stress response.

U.S. Pat. No. 6,211,142 discloses compositions comprising functionally active gas6 variants which are less γ carboxylated than gas6 derived from an endogenous source and articles of manufacture comprising the same for activation of the Rse receptor protein tyrosine kinase and promotion of the proliferation, survival and/or differentiation of cells comprising the Rse receptor such as neurons and glial cells.

CA2909669A1 discloses compositions and methods for treating viral infection in a mammal by administering a therapeutic dose of a pharmaceutical composition that inhibits AXL, MER or Tyro3 protein activity, for example by inhibition of the binding interaction between AXL, MER or Tyro3 and its ligand GAS6. Also disclosed are methods of treating, reducing, or preventing a phosphatidylserine harboring virus infection in a mammalian patient by administering one or more inhibitors of AXL, MER and/or Tyro3 activity, inhibitors of GAS6 activity or inhibitors of AXL, MER or Tyro3-GAS6 interaction.

JP 5478285 B2 discloses targeting tumor vasculature using conjugates that bind to phosphatidylserine. Targeting agents disclosed include anti-phosphatidylserine antibodies or antigen binding fragments thereof, annexin or phosphatidylserine-binding fragments to kill the tumor vascular endothelial cells to induce coagulation in the tumor vasculature or to induce tumor necrosis and/or tumor regression by destroying the vasculature of the tumor.

JP 4743672 B2 also discloses anti-phosphatidylserine antibodies as cancer treatments killing tumor vascular endothelial cells, inducing coagulation in the tumor vasculature or inducing tumor necrosis and or tumor regression by destroying the vasculature of the tumor.

U.S. Pat. No. 6,312,694 discloses aminophospholipid targeted diagnostic and therapeutic antibody-therapeutic agent constructs for use in tumor intervention.

Kimani et al. (Scientific Reports 2017 7:43908) disclose small molecule inhibitors that target the extracellular domain of Axl at the interface of the Ig-1 ectodomain of Axl and Lg-1 of Gas6 effectively blocking Gas6-inducible Axl receptor activation and suppressing H1299 lung cancer tumor growth in a mouse xenograft NOD-SCID γ model.

Preclinical studies have also been performed on a panel of PS-targeting antibodies that bind to PS with high affinity, either directly or when complexed to the serum protein β2-glycoprotein 1 (DeRose et al. Immunotherapy 2011 3:933-944: Huang et al. Cancer Res. 2005 65:4408-4416). These antibodies were shown to target endothelial cells in the tumor microenvironment (Ran et al. Cancer Res. 2002 62:6132-6140), to exhibit anti-tumor activity (de Freitas Balanco et al. Curr. Biol. 2001 11:1870-1873), and to enhance the activity of standard therapies in multiple preclinical tumor models (Beck et al. Int. J. Cancer 2005 118:2639-2643; He et al. Clin. Cancer Res. 2009 15:6871-6880).

In addition, the PS-targeting antibody, bavituximab, has been assessed in multiple clinical trials (Chalassani et al. Cancer Med. 2015 4:1051-1059; Digumarti et al. Lung Cancer 2014 86:231-236; and Gerber et al. Clin. Cancer Res. 2011 17:6888-6896). However, despite excitement surrounding the promise of PS-targeting monoclonal antibodies (mAbs), the latest phase III SUNRISE clinical trials of Peregrine Pharmaceuticals have led to underwhelming outcomes, resulting in discontinuation of new patient recruitment in 2016. Further studies have begun to evaluate the therapeutic efficacy of this antibody in combination with an anti-PD-L1 antibody for the treatment of solid tumors (globenewswire with the extension .com/news-release/2017/06/05/1008110/0/en/Peregrine-Pharmaceuticals-Presents-Preliminary-Correlative-Analysis-of-PD-L1-Expression-from-SUNRISE-Trial-at-ASCO-2017.html of the world wide web, Jun. 5, 2017).

There is a need to develop more efficacious PS-targeting derivatives as second or next generation immunobiologicals.

SUMMARY

An aspect of the present invention relates to a fusion molecule comprising a cytokine and a polypeptide which targets the fusion molecule to phosphatidylserine (PS).

In one nonlimiting embodiment, the polypeptide of the fusion molecule comprises a PS-binding ligand of Tyro3, Axl and Mer receptors, also referred to herein as a TAM ligand.

In one nonlimiting embodiment, the polypeptide of the fusion molecule comprises a PS-binding type domain of growth arrest-specific gene 6 (GAS6) or protein S (Pros1).

In one nonlimiting embodiment, the cytokine of the fusion molecule is an immune-stimulatory cytokine.

In another nonlimiting embodiment, the cytokine of the fusion molecule is an immune-suppressive cytokine.

Another aspect of the present invention relates to pharmaceutical compositions comprising a fusion molecule of the present invention.

Another aspect of the present invention relates to a method for targeting a cytokine to a pathological site in a subject by administering a fusion molecule or pharmaceutical composition comprising a fusion molecule of the present invention.

Another aspect of the present invention relates to a method for inhibiting immunosuppression which occurs from PS recognition by endogenous PS ligands and receptors at a pathological site in a subject by administering a fusion molecule or pharmaceutical composition comprising a fusion molecule of the present invention.

Another aspect of the present invention relates to a method for activating one or more cytokine-specific biological activities at a pathological site by administering a fusion molecule or pharmaceutical composition comprising a fusion molecule of the present invention.

Another aspect of the present invention relates to a method for minimizing systemic action of a cytokine by administering the cytokine via a fusion molecule or pharmaceutical composition comprising a fusion molecule of the present invention.

Yet another aspect of the present invention relates to a method for treating a disease, disorder or condition responsive to cytokine treatment by administering a fusion molecule or pharmaceutical composition comprising a fusion molecule of the present invention.

In one nonlimiting embodiment, the disease, disorder or condition treated with the present invention is cancer, infection or an inflammatory condition or disorder.

BRIEF DESCRIPTION OF THE FIGURES

FIG. 21A is an immunoblot showing the γ-carboxylation of Gas6(Gla)-IFN-λ2 and Gas6(Gla+EGF)—IFN-λ2 fusion molecules secreted from the EO771, a mouse breast cancer cell line stably expressing fusion molecules, following treatment with vitamin-K (Vit. K) or warfarin (Warf), a γ-carboxylation inhibitor. FIG. 21B shows results of tumor volume measurement following injection of $0.1 \times 10^6$ EO771 mock-transfected (empty vector) or Gas6(Gla+EGF)-IFN-22 fusion molecule secreting cells into the mammary fat-pad of C57BL/6 mice.

DETAILED DESCRIPTION

Figure 1:
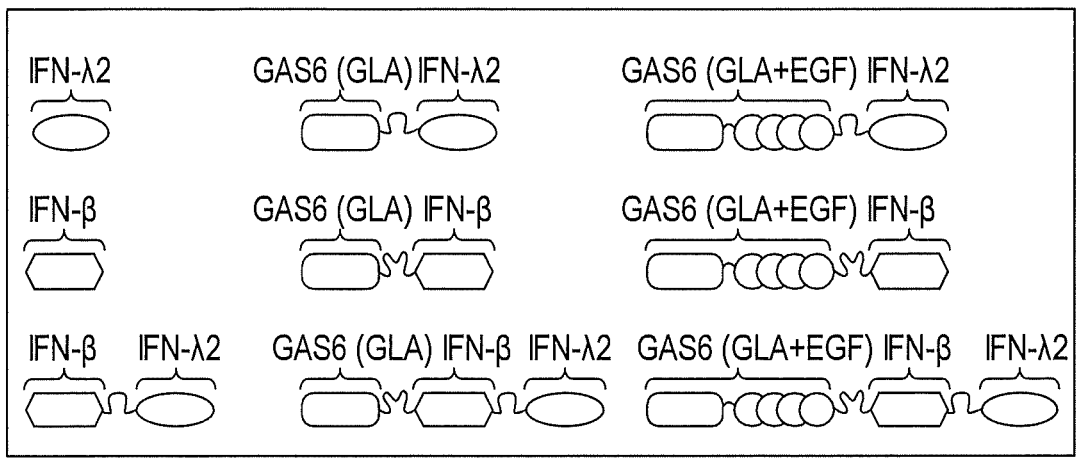
FIG. 1 provides diagrams of various nonlimiting embodiments of the fusion molecules of the present invention. In particular, nonlimiting schematic illustrations of the recombinant IFN fusion molecules and Gas6-IFN fusion molecules containing PS binding Gla domain and EGF repeats of Gas6 are provided. Gas6-IFN fusion molecules are designed to redirect immunosuppressive signals into immunogenic signals that activate host anti-tumor immunity. Linker sequences and variations are defined in the application.

While the immune system has the potential to eliminate pathogenic cells such as tumor cells, viruses and inflammatory cells involved in inflammatory disorders, a major barrier to effective immunotherapy is the ability to elicit a clinically meaningful response. To do so, the host must be capable of overcoming the intrinsic suppressive mechanisms that limit the development of effective immune responses.

Cytokines are powerful regulators of a variety of immune functions and can be used to treat a broad range of pathological conditions, including cancer, infections, and immune and inflammatory disorders. Due to undesirable side effects that accompany systemic administration of many cytokines, targeting cytokines to the sites with pathologies to achieve localized action of cytokines is highly preferable.

Externalization of phosphatidylserine (PS) is a hallmark of cancer cells themselves, and dys-regulated PS externalization in the tumor microenvironment (TME) has been observed in a wide range of human cancers making it a hallmark of all solid cancers. Dys-regulated PS in the TME can occur on a variety of cell types including apoptotic tumor cells, stressed tumor and various tumor-infiltrating cells resulting from hypoxia and nutrient deprivation, and stressed vascular endothelial cells at the tumor site.

Further, cells undergoing stress due to hypoxia and nutrient deprivation due to infections and/or inflammatory conditions also externalize PS. Moreover, enveloped viruses expose PS on their surfaces.

Therefore, targeting cytokines to PS-rich areas serves as a way of delivering cytokines to tumor sites, sites of viral infection and sites of inflammation, while minimizing their systemic action.

PS concentration on the cell surface appears to reflect the cellular stress level; and the changes in the PS concentration are sensed by a group of receptors collectively known as TAMs (Tyro3, Axl and Mer), which are activated by PS-binding TAM ligands Gas6 and Pros1. These ligands serve as bridging molecules, which interact with PS through their N-terminal Gla domains, and bind and activate TAMs through their C-terminal LG domains. Activation of TAMs is strictly PS-dependent and PS concentration acts as a rheostat for the intensity of TAM activation.

The present invention provides engineered bifunctional PS-targeting-cytokine fusion immunobiologics and methods for their use in targeting cytokines to tumor sites, sites of viral infection and sites of inflammation. Unlike PS-targeting mAbs that bind PS and passively block PS interactions with cognate receptors on tumor and myeloid cells, the fusion molecules of the present invention are designed to be able to tune the intensity of immunostimulatory cytokine signaling to PS concentration in the PS-rich microenvironment. Therefore, in the presence of PS, these PS-targeting-cytokine fusion molecules induce stronger and sustained cytokine receptor activation resulting in enhanced biological activities of the PS-targeting-cytokine fusion molecules in comparison to unmodified cytokines.

Moreover, activation of PS receptors, which can be triggered by direct binding to PS or by PS-interacting ligands, leads to the state of immunosuppression that is commonly established and maintained during, for example, tumor development.

The PS-targeting-cytokine fusion molecules of the present invention are expected to revert and redirect the state of immunosuppression by providing immune activation through cytokine-specific activities and by competing for PS binding with endogenous PS ligands and receptors, therefore blocking their ability to induce immunosuppressive state.

Accordingly, the bi-functional PS-targeting-cytokine fusion molecules of the present invention are expected to bind PS on stressed cells and localize immunostimulatory cytokine signaling to regions of high-externalized PS density. In doing so, the fusion molecules of the present invention are expected to redirect tolerogenic signals, which are generated through continuous engagement of immunosuppressive PS receptors, into immunogenic signals from the PS→cytokine receptor axis.

Thus, provided by the present invention are fusion molecules comprising a cytokine or portion thereof and a polypeptide which targets the fusion protein to PS. The developed fusion molecules of the present invention feature three unique characteristics in that they provide PS-targeted localized cytokine delivery; they block PS recognition by endogenous PS ligands and receptors; and by activating cytokine-specific biological activities, they actively change the immune activation balance from PS-induced immunosuppression to immune-activation that is tuned to the levels of PS. Accordingly, also provided by the present invention are pharmaceutical compositions comprising these fusion molecules as well as methods for use of the fusion molecules and pharmaceutical compositions in targeting a cytokine to a pathological site in a subject, inhibiting immunosuppression which occurs from PS recognition by endogenous PS ligands at a pathological site in a subject, activating one or more cytokine-specific biological activities at a pathological site, minimizing systemic action of a cytokine, and/or treating a disease, disorder or condition responsive to cytokine treatment. In one nonlimiting embodiment, the disease, disorder or condition targeted and/or treated with the present invention is cancer, infection or an inflammatory condition or disorder.

For purposes of the present invention, the terms "fusion protein" and "fusion molecule" are used interchangeably and are meant to encompass polypeptides, proteins and/or molecules made of parts from different sources. Such fusion molecules are created through the joining of two or more genes or fragments thereof that originally coded for separate proteins or portions thereof. Translation of these fused genes or portions thereof results in single or multiple polypeptides with functional properties derived from each of the original proteins. In one nonlimiting embodiment, the fusion molecules or proteins are created artificially by recombinant DNA technology for use in biological research or therapeutics.

For purposes of the present invention, by "portion thereof" it is meant a fragment shorter in length than the full length cytokine protein and which maintains at least a portion of the functional activity to the full length protein and/or binding to at least one of the receptor subunits.

Various immunostimulatory or immunosuppressive cytokines or portions thereof known to those skilled in the art can be included in the fusion molecules of the present invention. In a one nonlimiting embodiment, the cytokine selected has a desired activity at a pathogenic PS-rich site. In one nonlimiting embodiment, the cytokine is an interferon (IFN) or portion thereof. IFNs are pluripotent cytokines and play important roles in the establishment of a multifaceted antiviral response and anti-tumor response. Examples of cytokines which can be included in the fusion molecules of the present invention include, but are in no way limited to, interferon-α (IFN-α), interferon-β (IFN-β), interferon-2\1 (IFN-λ1), interferon-λ2 (IFN-λ2), interferon-λ3 (IFN-λ3), interferon γ (IFN-γ), interleukin 2 (IL-2), interleukin 10 (IL-10), interleukin 12 (IL-12), interleukin 15 (IL-15), interleukin 22 (IL-22), interleukin 33 (IL-33), amphiregulin (AREG), a combination thereof or a portion thereof. Some cytokines such as IFN-β, IFN-λ1, IFN-λ-2 and IFN-λ3 have unpaired Cys residues that can be substituted to improve folding and purification of the fusion molecules. Variants of cytokines with lower affinity to their corresponding receptors can be also used for the generation of the fusion PS-targeting cytokine proteins to reduce their signaling capabilities though their receptor complexes, and allowing enhancement of their activities in the presence of PS through the PS-mediated oligomerization of cytokine receptor complexes when activated by the fusion PS-targeting cytokines.

The fusion molecules of the present invention further comprise a polypeptide which targets the fusion molecule to PS. Various polypeptides targeting the fusion molecule to PS can be included in these fusion molecules. Examples of PS-targeting polypeptides which can be included in the fusion molecules of the present invention include, but are in no way limited to PS-binding domains of brain angiogenesis inhibitor 1 (BAI1), annexins, particularly annexin A5 and B12, T cell immunoglobulin and mucin receptor 1, 3 and 4 (TIM-1, TIM-3 and TIM-4), stabilin 1 and 2, and milk fat globule-EGF factor 8 protein (MFGE8). In one nonlimiting embodiment, the fusion molecule comprises a polypeptide comprising a PS-binding ligand of Tyro3, Axl and/or Mer (TAM) receptors. In one nonlimiting embodiment, the fusion molecule comprises a polypeptide comprising a PS-binding type domain of growth arrest-specific gene 6 (GAS6) or protein S (Pros1). In one nonlimiting embodiment, the fusion molecule comprises a polypeptide comprising an N-terminal Gla domain of Gas6 or Pros1. Nonlimiting examples of polypeptides useful in the fusion molecules of the present invention include:

Gla domain of mouse Gas6 with Signal Peptide and pro-domain:
(SEQ ID NO: 1)
MPPPPGPAAALGTALLLLLLASESSHTVLLRAREAAQFLRPRQRRA

YQVFEEAKQGHLERECVEEVCSKEEAREVFENDPETEYFYPRYQE;

Gla domain of mouse Gas6 with pro-domain without Signal Peptide:
(SEQ ID NO: 2)
TVLLRAREAAQFLRPRQRRAYQVFEEAKQGHLERECVEEVCSKEEA

REVFENDPETEYFYPRYQE;

-continued
Gla domain of mouse Gas6 without Signal peptide and pro-domain:
(SEQ ID NO: 3)
AYQVFEEAKQGHLERECVEEVCSKEEAREVFENDPETEYFYPRYQE;

Gla domain of human Gas6 with Signal Peptide and pro-domain:
(SEQ ID NO: 4)
MAPSLSPGPAALRRAPQLLLLLLAAECALAALLPAREATQFLRPRQ

RRAFQVFEEAKQGHLERECVEELCSREEAREVFENDPETDYFYPRY

LD;

Gla domain of human Gas6 with pro-domain without Signal Peptide:
(SEQ ID NO: 5)
ALLPAREATQFLRPRQRRAFQVFEEAKQGHLERECVEELCSREEAR

EVFENDPETDYFYPRYLD;

Gla domain of human Gas6 without Signal Peptide and pro-domain:
(SEQ ID NO: 6)
AFQVFEEAKQGHLERECVEELCSREEAREVFENDPETDYFYPRYLD;

Gla domain of human Pros1 with Signal Peptide and pro-domain:
(SEQ ID NO: 7)
MRVLGGRCGALLACLLLVLPVSEANFLSKQQASQVLVRKRRANSLL

EETKQGNLERECIEELCNKEEAREVFENDPETDYFYPKYLV;

Gla domain of human Pros1 with pro-domain without Signal Peptide:
(SEQ ID NO: 8)
NFLSKQQASQVLVRKRRANSLLEETKQGNLERECIEELCNKEEARE VFENDPETDYFYPKYLV;
and Gla domain of human Pros1 without Signal Peptide and pro-domain:
(SEQ ID NO: 9)
ANSLLEETKQGNLERECIEELCNKEEAREVFENDPETDYFYPKYLV.

Further, in some embodiments, the polypeptide which targets the fusion molecule to PS may further comprise a domain which promotes oligomerization of the PS-binding domain upon binding with PS. A nonlimiting example of a domain which promotes oligomerization of the PS-binding domain upon binding with PS which can be included in the fusion molecules of the present invention is epidermal growth factor (EGF)-like domains of GAS6 or Pros1. Nonlimiting examples include:

EGF-like domains of human GAS6
(SEQ ID NO: 10)
CINKYGSPYTKNSGFATCVQNLPDQCTPNPCDRKGTQACQDLMGNFF

CLCKAGWGGRLCDKDVNECSQENGGCLQICHNKPGSFHCSCHSGFEL

SSDGRTCQDIDECADSEACGEARCKNLPGSYSCLCDEGFAYSSQEKA

CRDVDECLQGRCEQVCVNSPGSYTCHCDGRGGLKLSQDMDTCE;
and

EGF-like domains of human Pros1
(SEQ ID NO: 11)
CLRSFQTGLFTAARQSTNAYPDLRSCVNAIPDQCSPLPCNEDGYMSC

KDGKASFTCTCKPGWQGEKCEFDINECKDPSNINGGCSQICDNTPGS

YHCSCKNGFVMLSNKKDCKDVDECSLKPSICGTAVCKNIPGDFECEC

PEGYRYNLKSKSCEDIDECSENMCAQLCVNYPGGYTCYCDGKKGFKL

AQDQKSCE.

Accordingly, in one nonlimiting embodiment, a fusion molecule of the present invention may comprise a polypeptide comprising an N-terminal PS-binding type domain and EGF-like oligomerization domains of GAS6 or Pros1. Nonlimiting examples of such fusion molecules include:

```
Gla domain and EGF-like domains of human Gas6
with Signal Peptide and pro-domain:
                                    (SEQ ID NO: 12)
MAPSLSPGPAALRRAPQLLLLLLAAECALAALLPAREATQFLRPRQR

RAFQVFEEAKQGHLERECVEELCSREEAREVFENDPETDYFYPRYLD

CINKYGSPYTKNSGFATCVQNLPDQCTPNPCDRKGTQACQDLMGNFF

CLCKAGWGGRLCDKDVNECSQENGGCLQICHNKPGSFHCSCHSGFEL

SSDGRTCQDIDECADSEACGEARCKNLPGSYSCLCDEGFAYSSQEKA

CRDVDECLQGRCEQVCVNSPGSYTCHCDGRGGLKLSQDMDTCE;

Gla domain and EGF-like domains of human Gas6
with pro-domain without Signal Peptide:
                                    (SEQ ID NO: 13)
ALLPAREATQFLRPRQRRAFQVFEEAKQGHLERECVEELCSREEARE

VFENDPETDYFYPRYLDCINKYGSPYTKNSGFATCVQNLPDQCTPNP

CDRKGTQACQDLMGNFFCLCKAGWGGRLCDKDVNECSQENGGCLQIC

HNKPGSFHCSCHSGFELSSDGRTCQDIDECADSEACGEARCKNLPGS

YSCLCDEGFAYSSQEKACRDVDECLQGRCEQVCVNSPGSYTCHCDGR

GGLKLSQDMDTCE;

Gla domain and EGF-like domains of human Gas6
without Signal Peptide and pro-domain:
                                    (SEQ ID NO: 14)
AFQVFEEAKQGHLERECVEELCSREEAREVFENDPETDYFYPRYLDC

INKYGSPYTKNSGFATCVQNLPDQCTPNPCDRKGTQACQDLMGNFFC

LCKAGWGGRLCDKDVNECSQENGGCLQICHNKPGSFHCSCHSGFELS

SDGRTCQDIDECADSEACGEARCKNLPGSYSCLCDEGFAYSSQEKAC

RDVDECLQGRCEQVCVNSPGSYTCHCDGRGGLKLSQDMDTCE;

Gla domain and EGF-like domains of human Pros1
with Signal Peptide and pro-domain:
                                    (SEQ ID NO: 15)
MRVLGGRCGALLACLLLVLPVSEANFLSKQQASQVLVRKRRANSLLE

ETKQGNLERECIEELCNKEEAREVFENDPETDYFYPKYLVCLRSFQT

GLFTAARQSTNAYPDLRSCVNAIPDQCSPLPCNEDGYMSCKDGKASF

TCTCKPGWQGEKCEFDINECKDPSNINGGCSQICDNTPGSYHCSCKN

GFVMLSNKKDCKDVDECSLKPSICGTAVCKNIPGDFECECPEGYRYN

LKSKSCEDIDECSENMCAQLCVNYPGGYTCYCDGKKGFKLAQDQKSC

E;

Gla domain and EGF-like domains of human Pros1
with pro-domain without Signal Peptide:
                                    (SEQ ID NO: 16)
NFLSKQQASQVLVRKRRANSLLEETKQGNLERECIEELCNKEEAREV

FENDPETDYFYPKYLVCLRSFQTGLFTAARQSTNAYPDLRSCVNAIP

DQCSPLPCNEDGYMSCKDGKASFTCTCKPGWQGEKCEFDINECKDPS

NINGGCSQICDNTPGSYHCSCKNGFVMLSNKKDCKDVDECSLKPSIC

GTAVCKNIPGDFECECPEGYRYNLKSKSCEDIDECSENMCAQLCVNY

PGGYTCYCDGKKGFKLAQDQKSCE;

and

Gla domain and EGF-like domains of human Pros1
without Signal Peptide and pro-domain:
                                    (SEQ ID NO: 17)
ANSLLEETKQGNLERECIEELCNKEEAREVFENDPETDYFYPKYLVC

LRSFQTGLETAARQSTNAYPDLRSCVNAIPDQCSPLPCNEDGYMSCK

DGKASFTCTCKPGWQGEKCEFDINECKDPSNINGGCSQICDNTPGSY

HCSCKNGFVMLSNKKDCKDVDECSLKPSICGTAVCKNIPGDFECECP

EGYRYNLKSKSCEDIDECSENMCAQLCVNYPGGYTCYCDGKKGFKLA

QDQKSCE.
```

In some nonlimiting embodiments of the present invention, the fusion molecule comprises type I and type III IFN proteins or portions thereof. Type I IFN proteins for use in the fusion molecule of the invention include but are not limited to IFN-α (alpha), IFN-β (beta), IFN-κ (kappa), IFN-ε (epsilon), and IFN-ω (omega) or portions thereof. Nonlimiting exemplary mature type I IFN proteins are:

human IFN-α2a:
(SEQ ID NO: SEQ ID NO: 18)
CKSSCSVGCDLPQTHSLGSRRTLMLLAQMRRISLFSCLKDRHDFGFP
QEEFGNQFQKAETIPVLHEMIQQIFNLFSTKDSSAAWDETLLDKFYT
ELYQQLNDLEACVIQGVGVTETPLMKEDSILAVRKYFQRITLYLKEK
KYSPCAWEVVRAEIMRSFSLSTNLQESLRSKE;

and human IFN-β:
(SEQ ID NO: 19)
MSYNLLGFLQRSSNFQCQKLLWQLNGRLEYCLKDRMNFDIPEEIKQL
QQFQKEDAALTIYEMLQNIFAIFRQDSSSTGWNETIVENLLANVYHQ
INHLKTVLEEKLEKEDFTRGKLMSSLHLKRYYGRILHYLKAKEYSHC
AWTIVRVEILRNFYFINRLTGYLRN.

Type III IFNs include IFN-λ1, IFN-λ2, IFN-λ3 and IFN-λ4 and portions thereof. Nonlimiting exemplary type III IFN proteins are:

human IFN-λ1:
(SEQ ID NO: 20)
PVPTSKPTPTGKGCHIGRFKSLSPQELASFKKARDALEESLKLKNWS
CSSPVFPGNWDLRLLQVRERPVALEAELALTLKVLEAAAGPALEDVL
DQPLHTLHHILSQLQACIQPQPTAGPRPRGRLHHWLHRLQEAPKKES
AGCLEASVTFNLFRLLTRDLKYVADGNLCLRTSTHPEST;

and human IFN-λ3:
(SEQ ID NO: 21)
VPVARLRGALPDARGCHIAQFKSLSPQELQAFKRAKDALEESLLLKD
CKCRSRLFPRTWDLRQLQVRERPVALEAELALTLKVLEASADTDPAL
GDVLDQPLHTLHHILSQLRACIQPQPTAGPRTRGRLHHWLYRLQEAP
KKESPGCLEASVTFNLFRLLTRDLNCVASGDLCV.

In some embodiments of the present invention, the fusion molecule may further comprise a linker between the cytokine and the polypeptide which targets the fusion molecule to PS. Linkers of use in the instant fusion molecule are preferably flexible and have a length in the range of 5-50 amino acids, or more preferably 10-30 amino acids. In certain embodiments, the linker element is a glycine/serine linker, i.e. a peptide linker substantially composed of the amino acids glycine and serine. Amino acids threonine or alanine can be also used within the linker. It will be clear to the skilled person that in cases in which the cytokine such as IFN on the N-terminal end of the fusion molecule already terminates with, e.g., a Gly, such a Gly may form the first Gly of the linker in the linker sequence. Likewise, in cases in which a cytokine such as IFN begins on the C-terminal with, e.g., a Pro, such a Pro residue may form the last Pro of the linker in the linker sequence. Examples of specific linker sequences are listed in Table 1. In particular embodiments, the linker of the fusion molecule of this invention is set forth in SEQ ID NO:42.

TABLE 1

| Linker Sequence | SEQ ID NO: |
|---|---|
| GSSGSSGSSGS | 22 |
| GSNGGFDSSEGG | 23 |
| SSGSSGSSGS | 24 |
| GSSGGSGGSGGG | 25 |
| GSSSDSDSSAGS | 26 |
| GSNDSGGSEGG | 27 |
| GSIRWSGLSGGD | 28 |
| GSRGGSVYSEGG | 29 |
| GSSEGSSDFGGD | 30 |
| GSIVVSCSSEGG | 31 |
| GSNWDSGCSREG | 32 |
| GSNWDSGCSREC | 33 |
| GSSGCTGDAGGS | 34 |
| GSNWDSGCSRQC | 35 |
| GSIAGCGDAGEG | 36 |
| GSNWDSGCSRE | 37 |
| GSNWDSGCSREG | 38 |
| NWDSGCSREG | 39 |
| IAGCGDAGEG | 40 |
| SRRASGSSGGSSGTSGSSGGSSGTSTDP | 41 |
| ASGSSGGSSGTSGSSGGSSGTS | 42 |
| ASGSSGGSSGTSGSSGGSSGTSTDP | 43 |
| GGGGS | 44 |
| GGGGSGGGGS | 45 |
| GGGGSGGGGSGGGGS | 46 |
| GSSGSSGSSGSGSSGSSGSSGS | 47 |
| ASGSSGGSSGTS | 48 |

Accordingly, in one nonlimiting embodiment, the fusion molecule of the present invention comprises a polypeptide comprising an N-terminal PS-binding type domain with Signal Peptide and pro-domain and EGF-like oligomerization domains of murine GAS6 fused to murine IFN-β and murine IFN-λ2 protein.

Gas6(Gla + EGF)-linker-IFN-β-linker-IFN-λ2
(Gas6(Gla + EGF)-IFN-β-IFN-λ2):
(SEQ ID NO: 49)
MPPPPGPAAALGTALLLLLLASESSHTVLLRAREAAQFLRPRQRRAY

QVFEEAKQGHLERECVEEVCSKEAREVFENDPETEYFYPRYQECMRK

YGRPEEKNPDFAKCVQNLPDQCTPNPCDKKGTHICQDLMGNFFCVCT

DGWGGRLCDKDVNECVQKNGGCSQVCHNKPGSFQCACHSGFSLASDG

QTCQDIDECTDSDTCGDARCKLPGSYSCLCDEGYTYSSKEKTCQDVD

ECQQDRCEQTCVNSPGSYTCHCDGRGGLKLSPDMDTCEASGSSGGSS

GTSGSSGGSSGTSINYRQLQLQERTNIRKSQELLEQLNGKINLTYRA

DFKIPMEMTEKMQKSYTAFAIQEMLQNVELVFRNNFSSTGWNETIVV

RLLDELHQQTVFLKTVLEEKQEERLTWEMSSTALHLKSYYWRVQRYL

KLMKYNSYAWMVVRAEIFRNFLIIRRLTRNFQNASGSSGGSSGTSGS

SGGSSGTSTDPVPRATRLPVEAKDCHIAQFKSLSPKELQAFKKAKDA

IEKRLLEKDMRCSSHLISRAWDLKQLQVQERPKALQAEVALTLKVWE

NMTDSALATILGQPLHTLSHIHSQLQTCTQLQATAEPKPPSRRLSRW

LHRLQEAQSKETPGCLEDSVTSNLFRLLTRDLKCVASGDQCV.

In another nonlimiting embodiment, the fusion molecule of the present invention comprises a polypeptide comprising an N-terminal PS-binding type domain with Signal Peptide and pro-domain and EGF-like oligomerization domains of human GAS6 fused to human IFN-β and human IFN-λ3 protein.

Gas6(Gla + EGF)-linker-IFN-β-linker-IFN-λ2
(Gas6(Gla + EGF)-IFN-β-IFN-λ2):
(SEQ ID NO: 50)
MAPSLSPGPAALRRAPQLLLLLLAAECALAALLPAREATQFLRPRQR

RAFQVFEEAKQGHLERECVEELCSREEAREVFENDPETDYFYPRYLD

CINKYGSPYTKNSGFATCVQNLPDQCTPNPCDRKGTQACQDLMGNFF

CLCKAGWGGRLCDKDVNECSQENGGCLQICHNKPGSFHCSCHSGFEL

SSDGRTCQDIDECADSEACGEARCKNLPGSYSCLCDEGFAYSSQEKA

CRDVDECLQGRCEQVCVNSPGSYTCHCDGRGGLKLSQDMDTCEASGS

SGGSSGTSGSSGGSSGTSMSYNLLGFLQRSSNFQCQKLLWQLNGRLE

YCLKDRMNFDIPEEIKQLQQFQKEDAALTIYEMLQNIFAIFRQDSSS

TGWNETIVENLLANVYHQINHLKTVLEEKLEKEDFTRGKLMSSLHLK

RYYGRILHYLKAKEYSHCAWTIVRVEILRNFYFINRLTGYLRNASGS

SGGSSGTSGSSGGSSGTSTDPVARLRGALPDARGCHIAQFKSLSPQE

LQAFKRAKDALEESLLLKDCKCRSRLFPRTWDLRQLQVRERPVALEA

ELALTLKVLEASADTDPALGDVLDQPLHTLHHILSQLRACIQPQPTA

GPRTRGRLHHWLYRLQEAPKKESPGCLEASVTENLERLLTRDLNCVA

SGDLCV.

Nonlimiting embodiments of various fusion molecules of the present invention are depicted in FIG. 1. Shown therein are embodiments comprising: a polypeptide which targets the fusion molecule to PS, a linker and a cytokine; a polypeptide which targets the fusion molecule to PS, a linker and a combination of two different cytokines; a polypeptide which targets the fusion molecule to PS further comprising a domain which promotes oligomerization of the PS-binding domain upon binding with PS linked thereto, a linker and a cytokine; and a polypeptide which targets the fusion molecule to PS further comprising a domain which promotes oligomerization of the PS-binding domain upon binding with PS linked thereto, a linker and a combination of two different cytokines.

Figure 2:
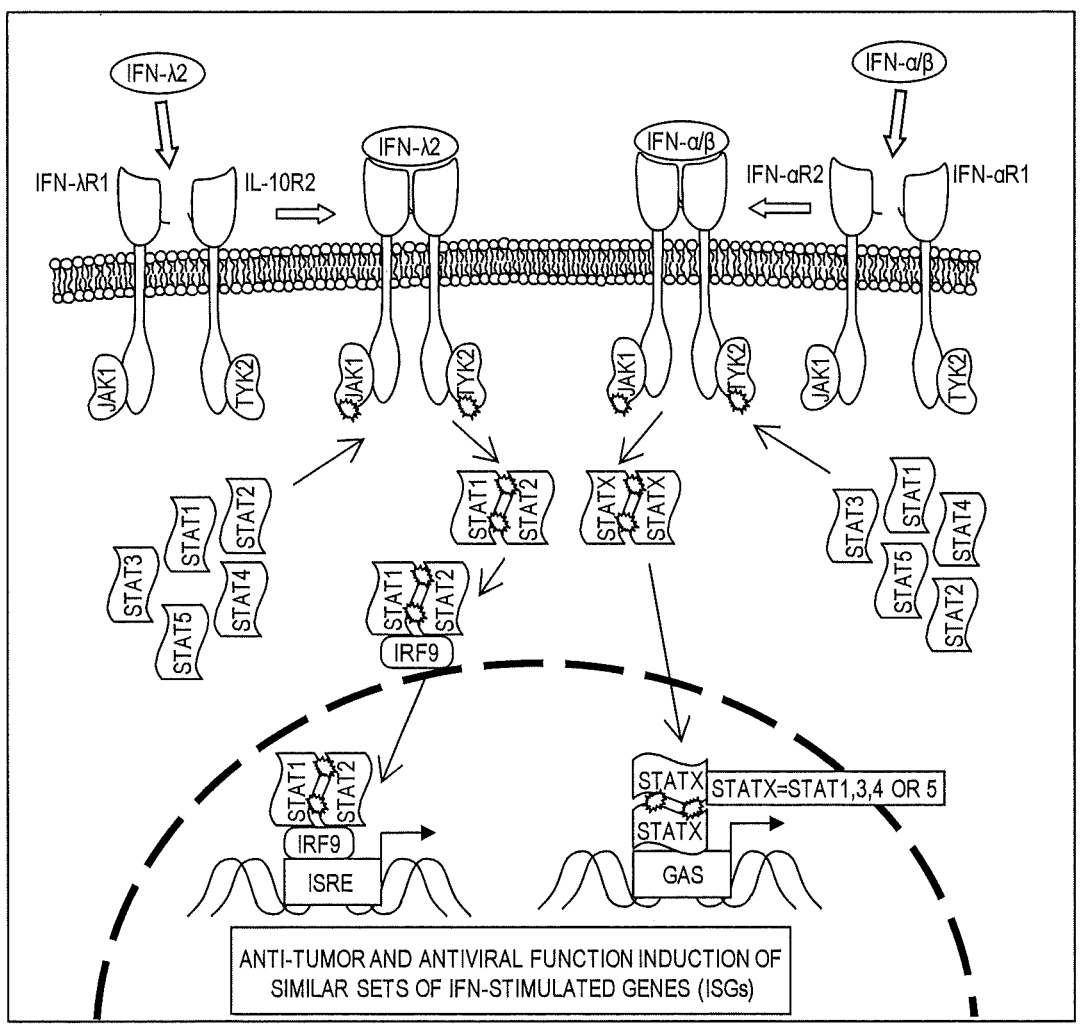
FIG. 2 depicts models of type III IFN (IFN-λ) and type I IFN (IFN-α/β) receptor systems. IFN-λs and type I IFNs use distinct heterodimeric receptor complexes. The IFN-λs engage the unique IFN-λR1 and IL-10R2, whereas IFN-αR1 and IFN-αR2 form the active type I IFN receptor complex. The engagement of IFN-α or IFN-λ receptors results in phosphorylation of receptor-associated JAK kinases JAK1 and Tyk2 and this is followed by phosphorylation of STAT1 and STAT2 that interact with a DNA-binding protein IRF9 leading to the formation of a transcriptional complex designated IFN-stimulated gene factor 3 (ISGF3), which binds to the IFN-stimulated response element (ISRE) and regulates transcription of IFN-stimulated genes (ISGs).

FIG. 2 depicts models of cytokine receptor complexes and signaling pathways exemplified herein by receptor systems for type III IFN (IFN-λ) and type I IFN (IFN-α/(3). IFN-λs and type I IFNs use distinct heterodimeric receptor complexes. The IFN-λs engage the unique IFN-λR1 and IL-10R2, whereas IFN-αR1 and IFN-αR2 form the active type I IFN receptor complex. The engagement of IFN-α or IFN-λ receptors results in phosphorylation of receptor-associated JAK kinases JAK1 and Tyk2 and this is followed by phosphorylation of STAT1 and STAT2 that interact with a DNA-binding protein IRF9 leading to the formation of a transcriptional complex designated IFN-stimulated gene factor 3 (ISGF3), which binds to the IFN-stimulated response element (ISRE) and regulates transcription of IFN-stimulated genes (ISGs).

Figure 3:
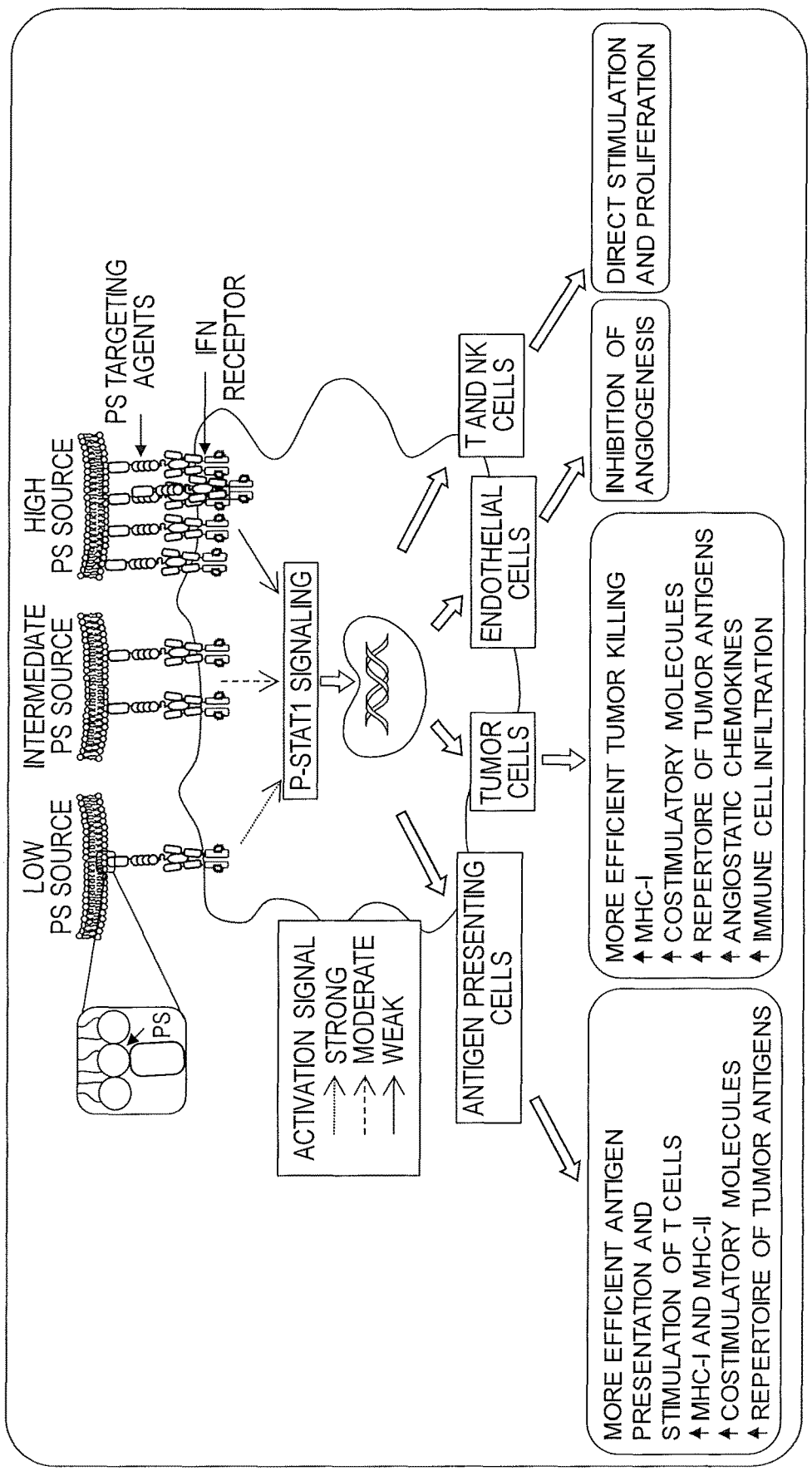
FIG. 3 provides a diagram of the proposed immunogenic function of Gas6-IFN-β and/or IFN-λ2 fusion molecules of the present invention in the PS-enriched tumor microenvironment or virus infection site. Gas6 (via its Gla and EGF-like domains) act as PS sensors and are proposed to respond to the magnitude of externalized PS in the tissue microenvironment. Gas6 will respond to the concentration of externalized PS and localize cytokines in a PS-dependent manner to tissues. At lower externalized PS concentrations, IFN activity is expected to be low (native cytokine activity) while at higher concentrations (in the tumor microenvironment or in virus infected cells/tissues), IFN activity is expected to be amplified and will enhance cytokine activity leading to improved anti-tumor immunity and antiviral response. Captions in the figures identify potential target cell types as well as expected phenotypic outcomes. For example, on tumor cells targeting of Gas6-IFNs is expected to lead to increased expression of MHC class I antigens and co-stimulatory molecules, leading to the increased expression/presentation of tumor antigens, increased production of angiostatic chemokines, and increased immune cell infiltration. On antigen presenting cells, Gas6-IFN fusion molecules are expected to increase MHC class I and MHC class II antigen expression, as well as increase dendritic cell maturation and increase cross-presentation of tumor antigens.

FIG. 3 provides a diagram of a nonlimiting embodiment of predicted binding and interaction of a fusion molecule of the present invention in a PS-rich environment such as a tumor microenvironment or a virus infection site. As depicted by FIG. 3, in the PS positive tumor microenvironment, the Gla domain of the Gas6 will bind directly to the PS on the apoptotic tumor cells or tumor vasculature, and immune-stimulatory cytokines such as IFN-β and/or IFN-λ2 will bind to their respective IFN-β and/or IFN-λ receptors on the antigen pressing cells (APCs), tumor cells, endothelial cells and other tumor-infiltrating cells. The mechanisms of IFN-mediated antitumor activities include direct action on tumor cells to: i) suppress their proliferation and promote their apoptosis, ii) promote production of inflammatory cytokines and chemokines leading to the increased recruitment of immune cells to the tumor, and iii) enhance antigen presentation by tumor cells achieved by the up-regulation of MHC class I molecules and co-stimulatory molecules, and changes in antigen processing leading to the altered and diversified repertoire of tumor antigens presented by the tumor cells, which in turn results in better recognition by the T cells. IFNs also inhibit tumor angiogenesis by directly inhibiting proliferation of endothelial cells and by promoting production of angiostatic chemokines by tumor cells and tumor-infiltrating immune cells. Moreover, IFNs exert a variety of immune-stimulatory activities on immune cells, which include: i) activation and enhanced antigen presentation by professional antigen-presenting cells (APCs) leading to the stimulation of T helper 1 (Th1) cell response; ii) stimulation of proliferation and differentiation of CD4+ and CD8+ T cells by directly acting on these cells; iii) direct stimulation of NK cells and promotion their antitumor activities. Further, the PS-targeting cytokines will compete for PS binding with endogenous PS ligands such as Gas6 and Pros1, and therefore block the ability of Gas6 and Pros1 to induce immunosuppressive signals through TAM receptors. The fusion molecules of the present invention will induce receptor clustering resulting in the strong pStat1 signaling as compared to IFN-β and IFN-λ2 alone. The fusion molecules of the present invention will thus serve the dual functions of targeted therapy and immunotherapy by binding to immunosuppressive PS molecules and inducing cytokine receptor mediated immunogenic signaling in the tumor microenvironment.

Figure 4:
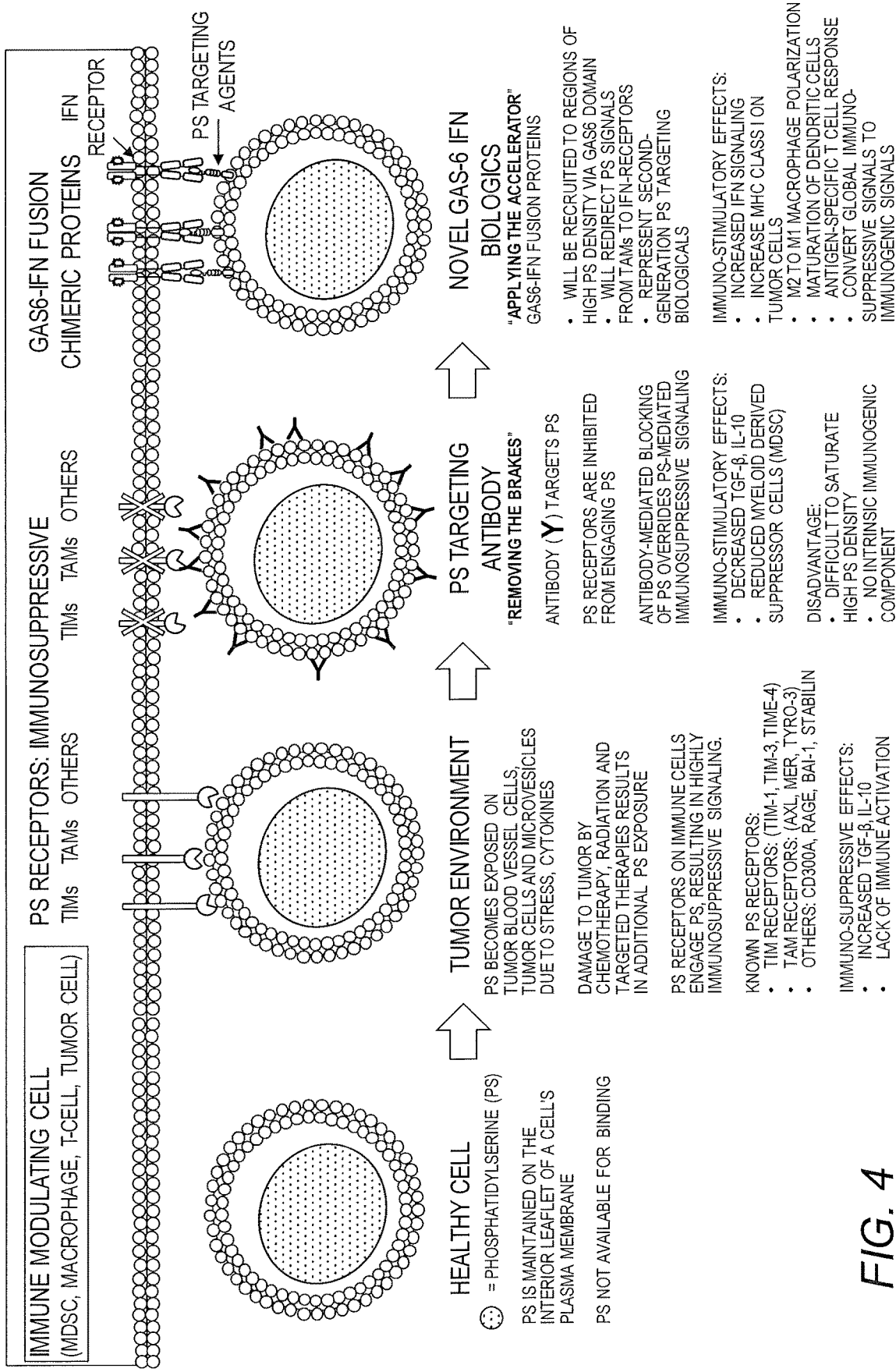
FIG. 4 depicts a rationale for "second-generation" PS-targeting biologics. To date, PS targeting mAbs have been developed to bind and essentially mask externalized PS. The Gas6-IFN fusion molecules developed herein are designed to target IFNs to the PS-rich TME and thereby convert tolerogenic signals into immunogenic signals. Moreover, since Gas6-targeted IFNs will induce PDL1, they are particularly well adopted for use as combinatorial therapeutics with anti-PD1/anti-PDL1. Attributes of the Gas6-IFN biologics are indicated under the caption.

The PS targeting molecules of the present invention were designed to bind PS, but rather than engaging immunosuppressive pathways through TAM receptors, they activate IFN receptors to induce host anti-tumor and antiviral immunity (FIG. 4).

Figure 5:
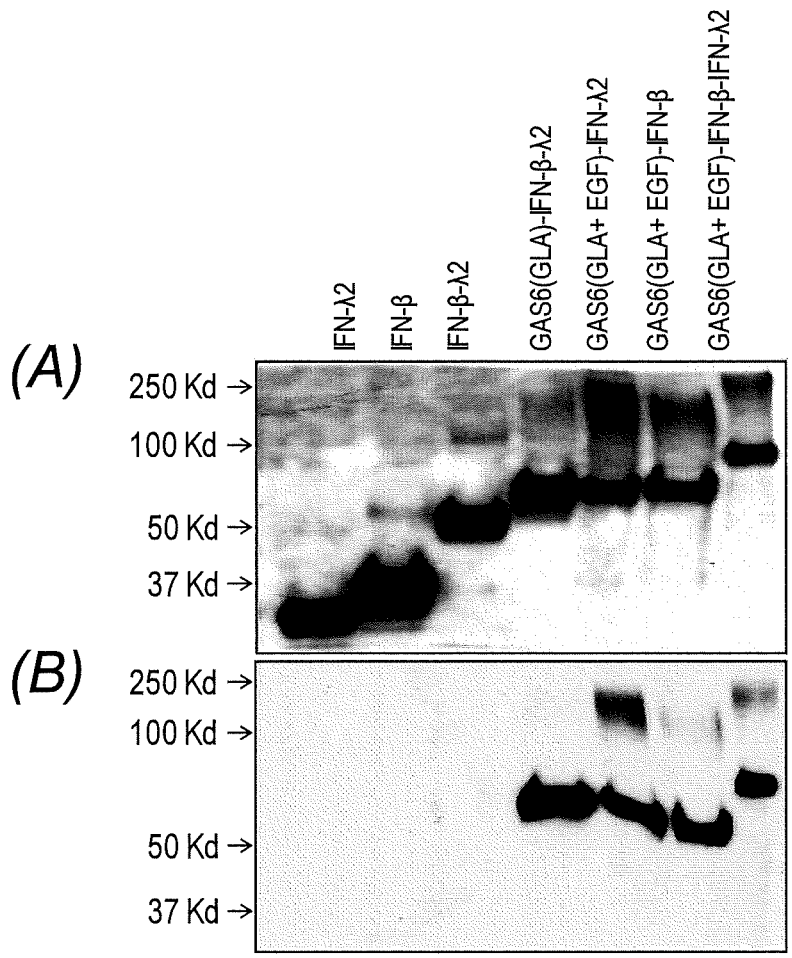
FIGS. 5(A) and (B) show generation, expression, and detection of His-tagged Gas-IFN proteins. The Gas6-IFN fusion molecules have been cloned and expressed in HEK293, E0771, and Expi293 cells (for larger scale production). Recombinant fusion molecules secretions into the cell supernatants of the HEK293T cell supernatant collected after 48 hours of transfection were analyzed by immunoblot using anti-His mAb and demonstrate the presence of the His-tagged proteins at the expected molecular weights (top panel; (A)). Immunoblot with anti-Gla mAb (bottom panel; (B)) shows the γ-carboxylation as probed with γ-carboxylation specific antibodies. As noted, all the Gas6 fusion molecules (last 4 lanes) become γ-carboxylated (a requisite for binding PS) when the cells are grown in the presence of Vitamin K using anti-Gla-specific mAb. These results indicate proteins are active as PS binding proteins, a requisite of the claims in the application.
Figure 6:
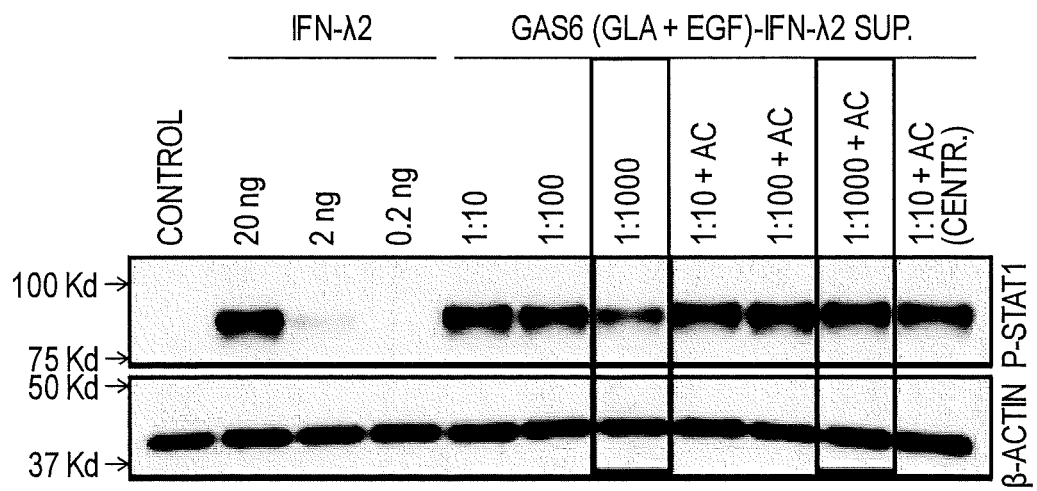
FIG. 6 shows activity of a Gas6-IFN-λ2 fusion molecule of the present invention as measured by detecting the degree of Stat1 activation (Tyr phosphorylation of Stat1, pStat1) by immunoblot in lysates of the IFN-λR-γR1 reporter cell line treated with recombinant IFN-λ2 or with HEK293T cell supernatant containing Gas6(Gla+EGF)-IFN-λ2 fusion molecules with or without apoptotic cells for 30 minutes. The pStat1 immunoblots showed PS-binding dependent enhancement of activation of the IFN-λ receptor by the fusion molecule particularly at the high concentration of PS (1:1000-reporter cells/apoptotic cells (AC); comparison of lanes 7 and 10).
Figure 7:
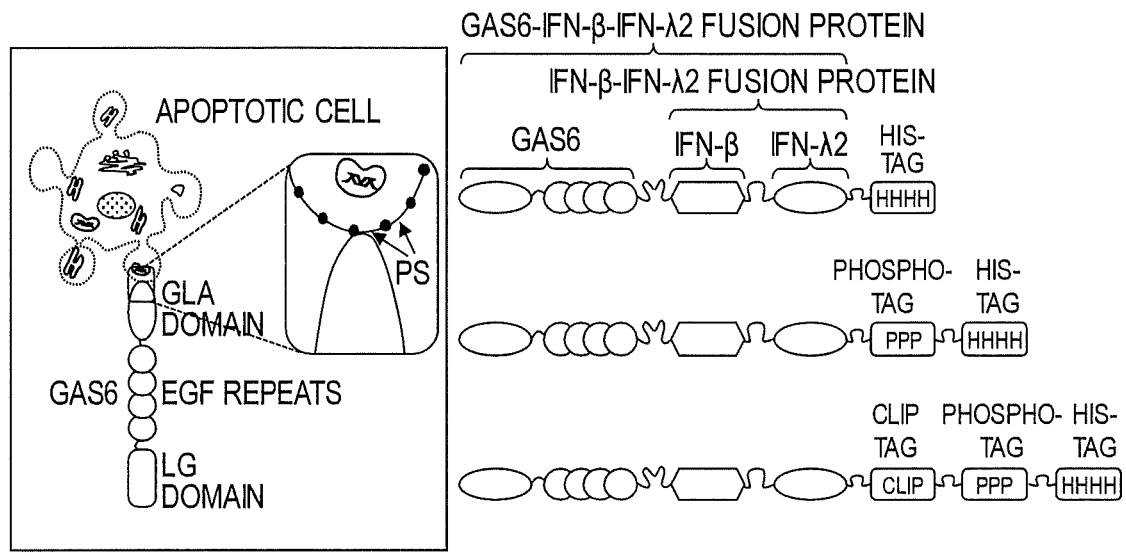
FIG. 7 provides schematic illustrations of the Gas6(Gla+EGF)-IFN-β-IFN-λ2 fusion molecules containing phospho-tag and CLIP tag labeling peptides for protein purification and detection. In addition to His-tagged proteins, a phosphorylation-tag (for $^{32}$P-labeling) and a CLIP tag (for fluorescent labeling proteins) were engineered to the fusion molecules containing type I and type III IFNs. These latter tags were introduced for in vivo labeling, utility, and localization. Left side of figure reiterates the domain structure of Gas6, including Gla binding region activity of the fusion molecules. Cell viability was measured using the MTT assay.
Figure 8:
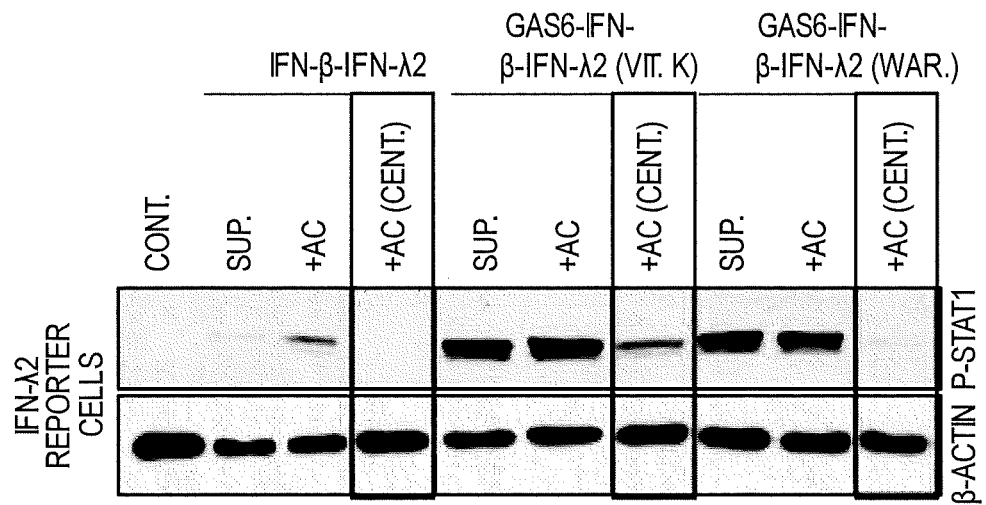

A series of 12 murine Gas6-IFN fusion molecules containing either Gla domain alone or both Gla and EGF-like domains (Gla+EGF) of Gas6 have been cloned and sequenced. Six murine Gas6-IFN fusion molecules are depicted in FIG. 1. Other variants included His-tagged proteins to facilitate their purification as well as tags enabling protein labeling for imaging protein distribution in vivo (FIG. 7). All chimeric proteins were subsequently expressed in HEK293T cells, shown to be secreted to the conditioned media, and are shown to be highly γ-carboxylated, an essential post-translational modification required for fusion molecules to bind PS when cells are cultured in the presence of Vitamin K. FIG. 5 depicts the presence of several His-tagged Gas6-IFN fusion molecules in the conditioned media of HEK293 cells transfected with the corresponding expression plasmids, demonstrating their production and secretion from the cells (FIG. 5(A)) and γ-carboxylation (FIG. 5(B)). Moreover, it was observed that the dimer formation was strongly promoted in the presence of Gas6-derived EGF repeats. All Gas6-IFN proteins retained biological activities as demonstrated by their ability to induce IFN signaling on reporter cell lines and all retained capacity to bind PS in a γ-carboxylation dependent manner. Further, the PS-binding domain of Gas6 (Gla-EGF-like domains) when fused with IFNs, allowed IFNs to induce stronger signaling in the presence of apoptotic cells suggesting that the intensity of IFN response triggered by Gas6-IFN fusion molecules is enhanced by increases in PS concentrations, as intended by the rationale and design (See FIGS. 6 and 8, and 19A through 19C). Moreover, only γ-carboxylated Gas6-IFN fusion molecules bind to apoptotic cells, because IFN activity was co-precipitated together with apoptotic cells only when Gas6-IFN fusion molecules were γ-carboxylated (FIG. 8).

Figure 16:
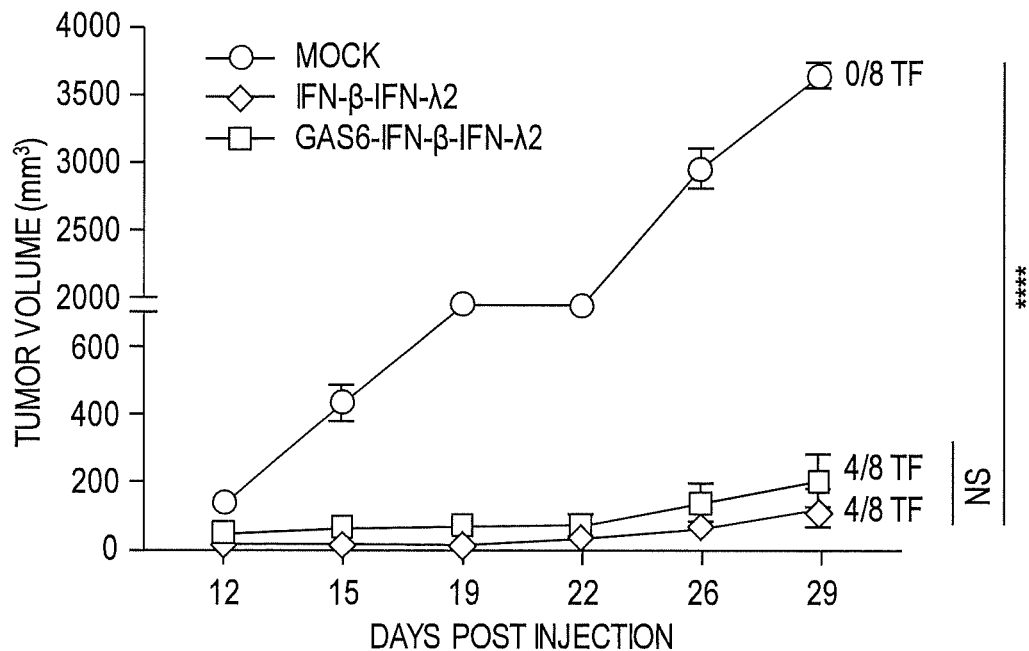
Figure 17:
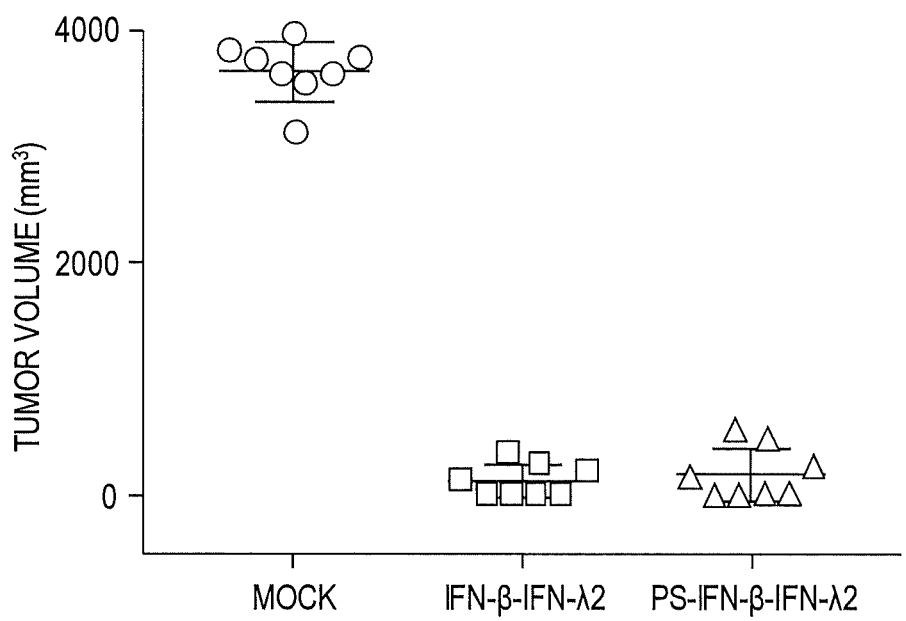
Figures 18, 19A:
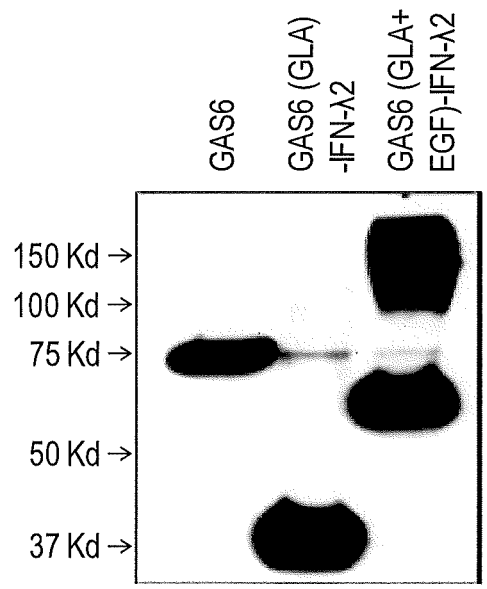
Figure 19B:
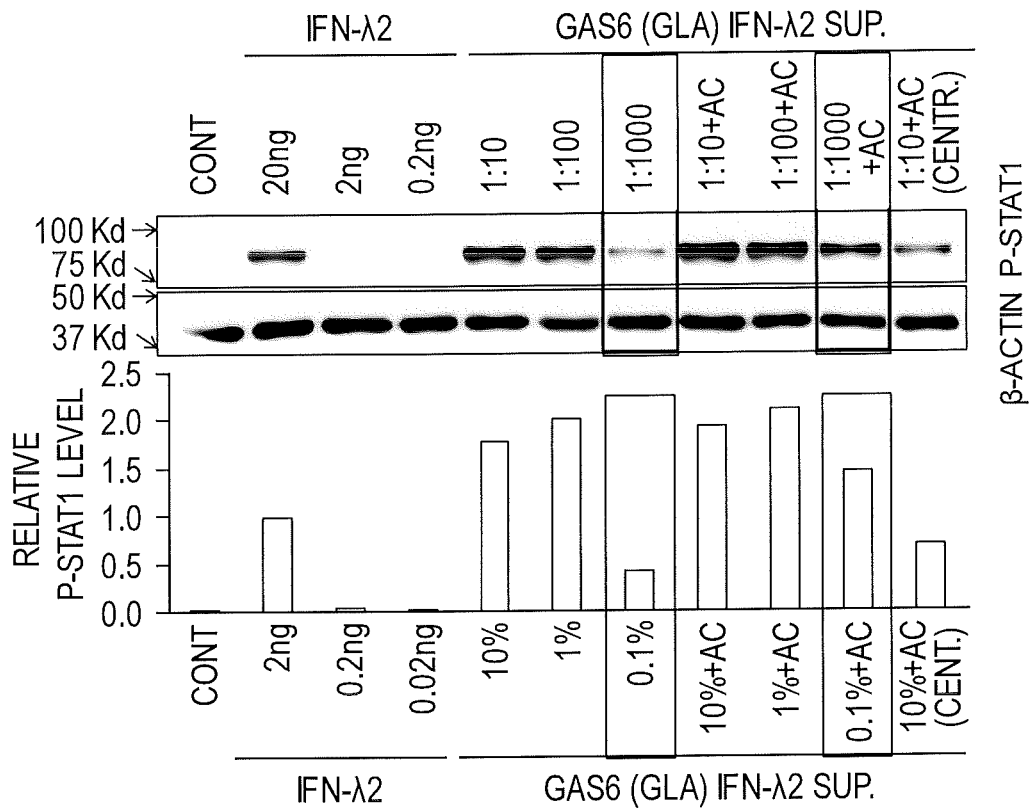
Figure 19C:
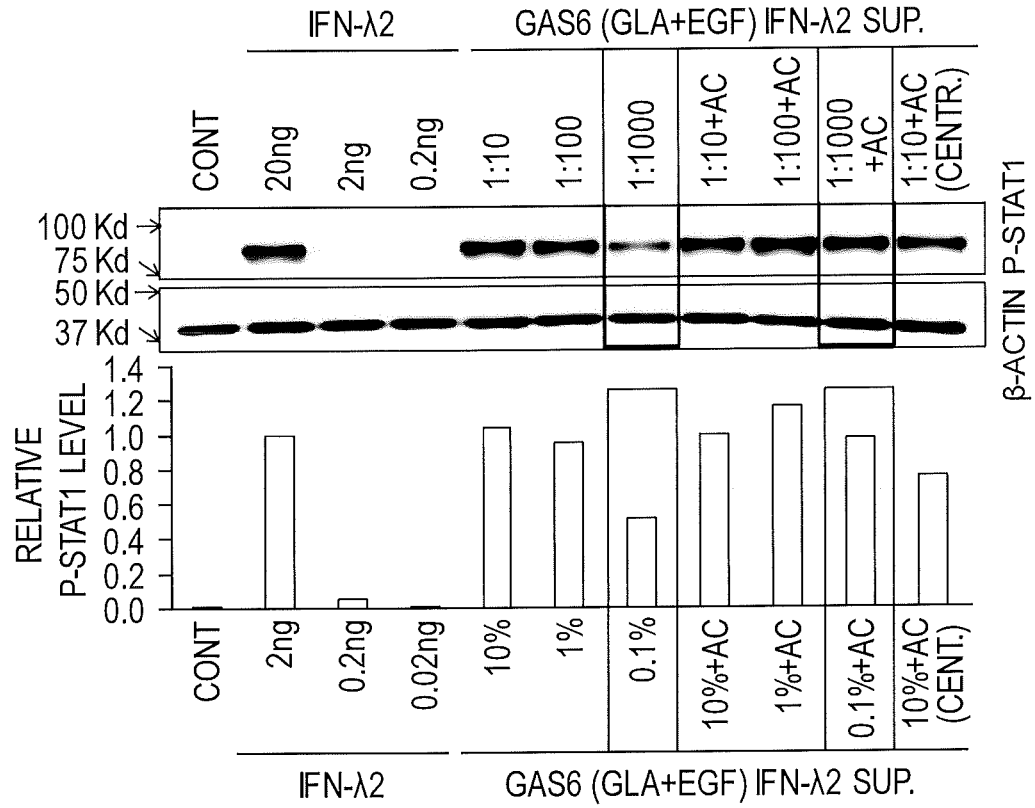
Figure 21A:
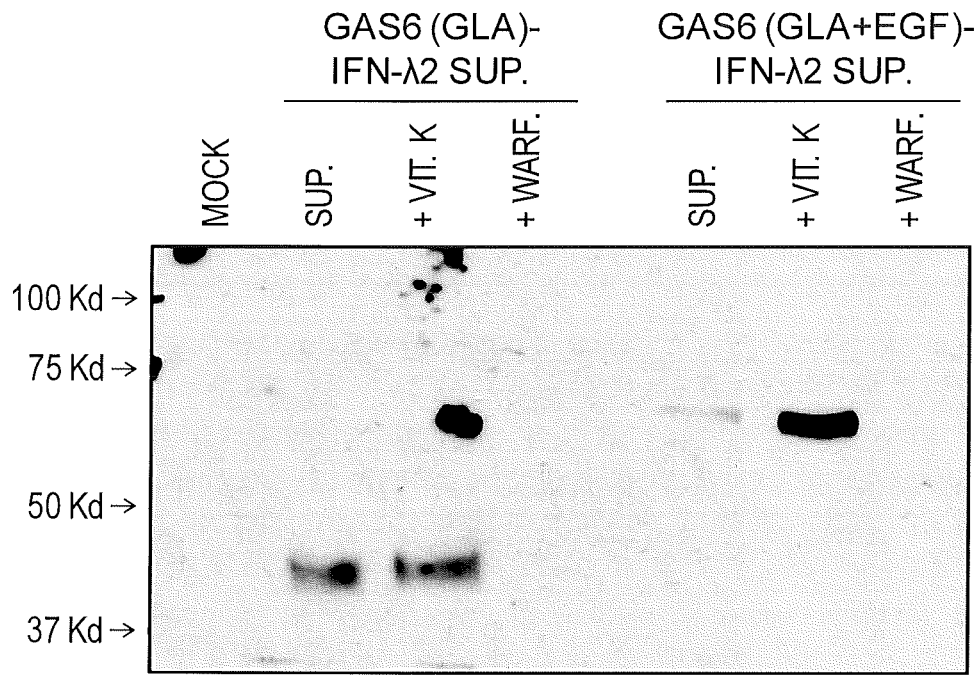
FIGS. 21A and 21B show the anti-tumor activity of the Gas6-IFN-λ2 fusion molecules of the present invention.
Figure 21B:
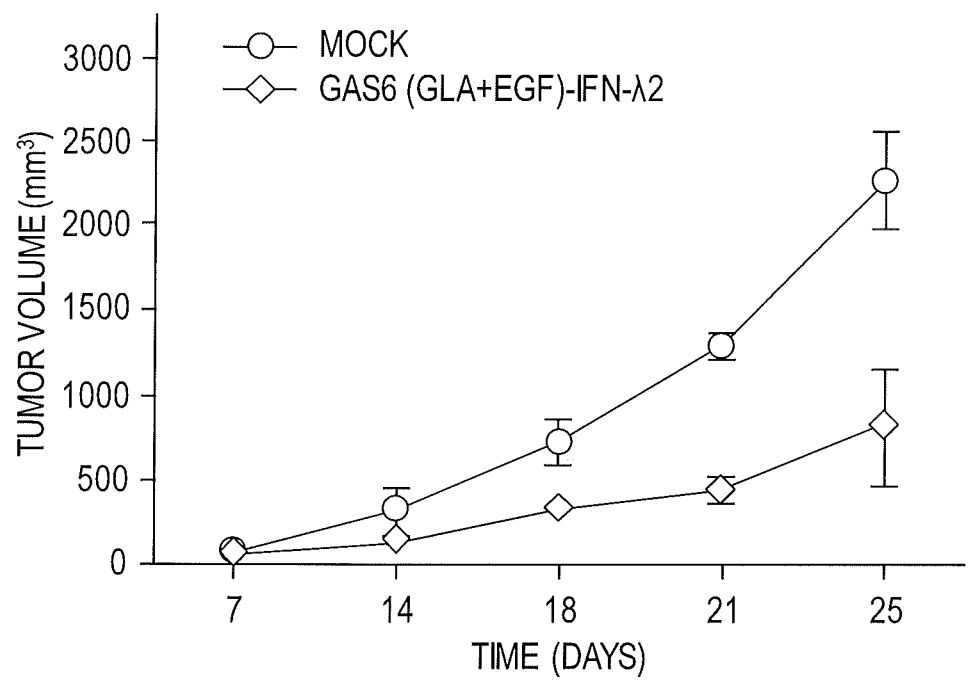

Further, mouse model of mammary tumor growth, in which murine breast cancer EO771 cells orthotopically transplanted into mammary fat pads, demonstrated that EO771 tumor cells constitutively expressing and secreting Gas6(Gla+EGF)-IFN-λ2 (see FIGS. 21A and 21B) and Gas6 (Gla+EGF)-IFN-β demonstrated growth retardation when injected into mammary fat-pad of the syngeneic immune-competent C57BL/6 mice. The Gas6(Gla+EGF)-IFN-λ2 fusion molecules showed a significant decrease in the tumor volume as compared to the controls, also referred to herein as mock. The secreted Gas6(Gla+EGF)-IFN-λ2 fusion molecule from EO771 cells has also been demonstrated in vitro to possess IFN-λ2 activity in the IFN-λ reporter cells. Further, mouse model of mammary tumor growth also demonstrated that Gas6(Gla+EGF)-IFN-β-IFN-λ2 fusion molecule has anti-cancer activities comparable to those of IFN-β-IFN-λ2 fusion molecule (FIGS. 16 and 17). In this model, EO771 mammary tumor cells constitutively expressing and secreting Gas6(Gla+EGF)-IFN-β-IFN-λ2 or IFN-β-IFN-λ2 molecules demonstrated growth retardation when injected into mammary fat-pad of the syngeneic immune-competent C57BL/6 mice. Tumor cells expressing either Gas6(Gla+EGF)-IFN-β-IFN-λ2 or IFN-β-IFN-λ2 fusion molecules showed a significant decrease in the tumor volume as compared to the mock-transfected tumor cells and four out of 8 mice in each group remained tumor free (FIGS. 16 and 17). Moreover, EO771 cells expressing Gas6-IFN-β-IFN-λ2 fusion molecule grew much slower in vivo than a 50:50 mixture of EO771 cells constitutively secreting Gas6-IFN-β and Gas6-IFN-λ2 individual proteins, demonstrating that the fusion Gas6-IFN-β-IFN-λ2 molecules have higher anti-tumor potency than the combination of individual PS-targeted type I and type III IFNs.

Figure 10:
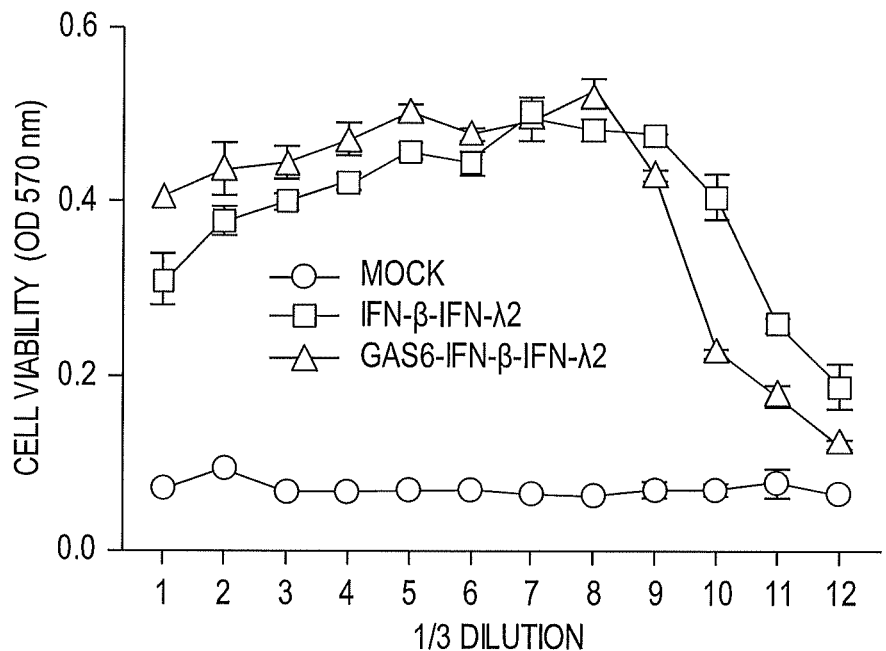
Figure 11:
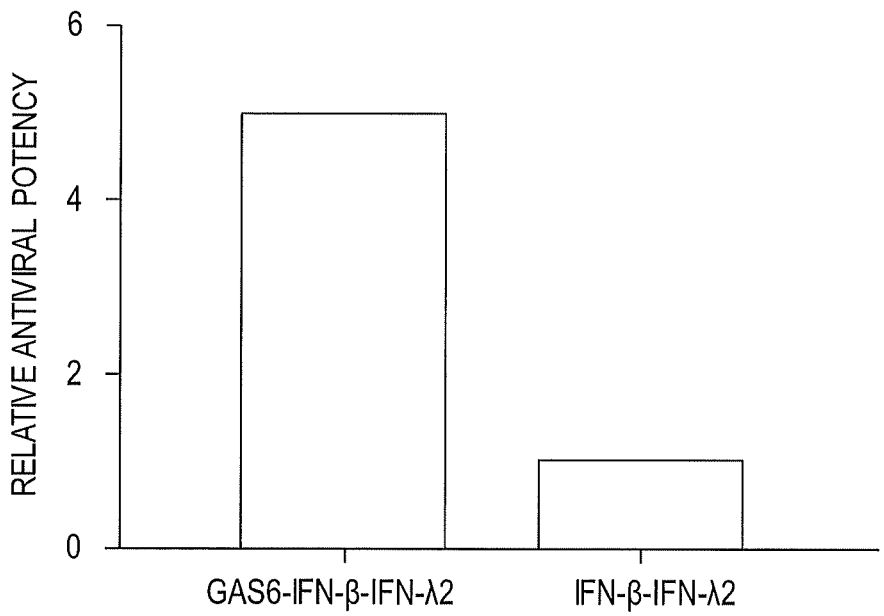
Figure 12:
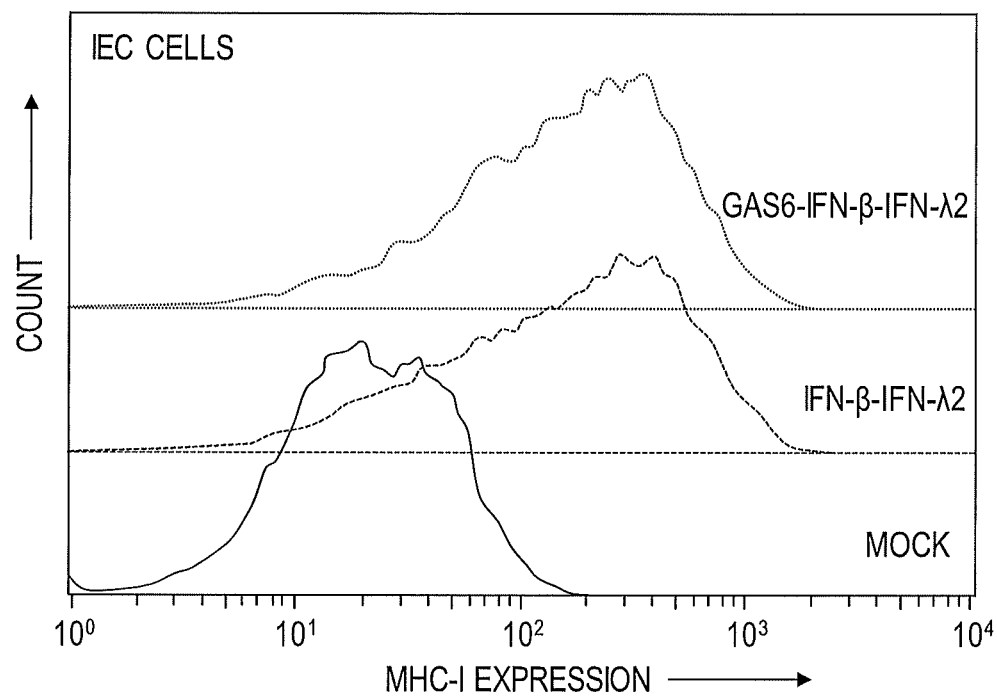
Figure 13:
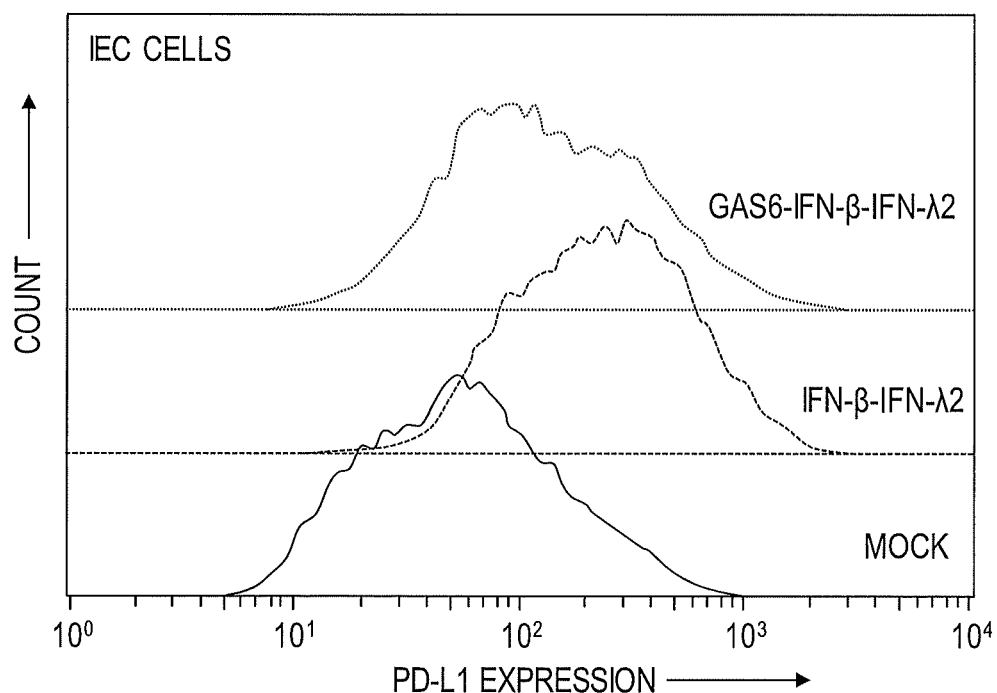
Figure 14:
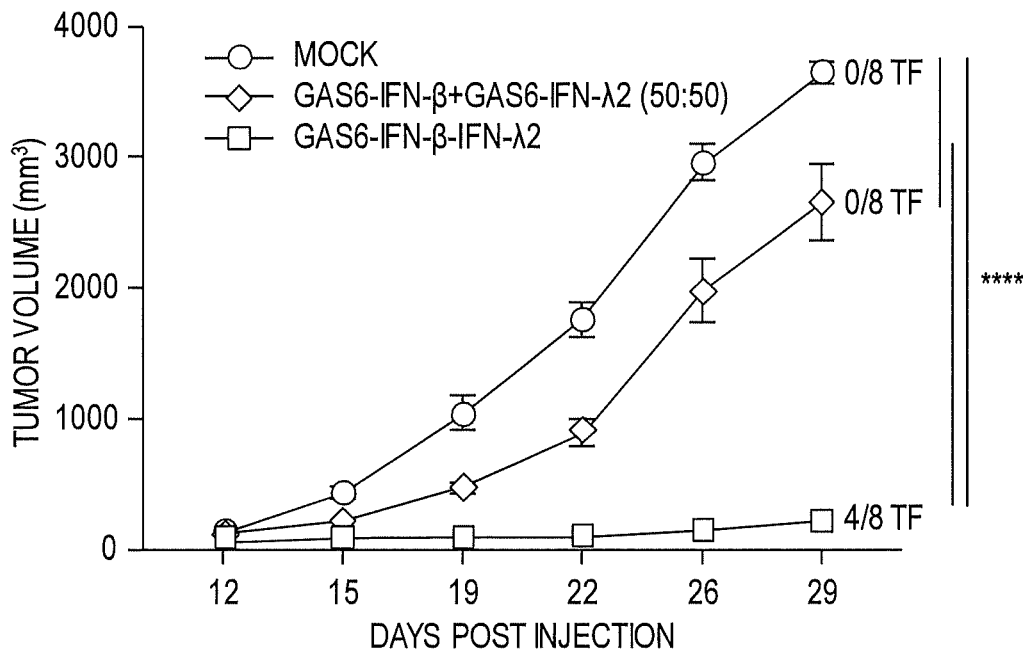
Figure 15:
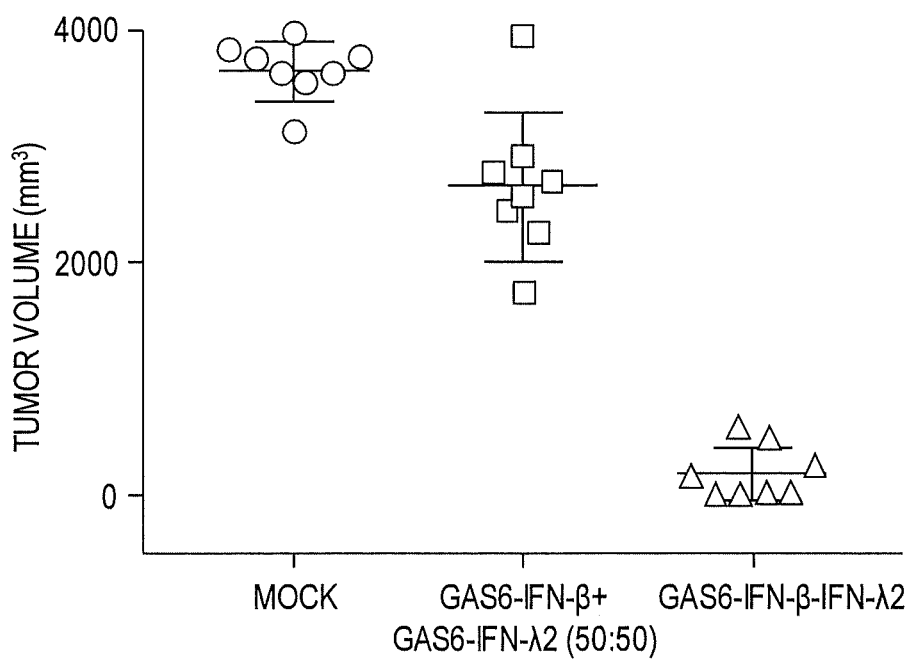
Figure 20A:
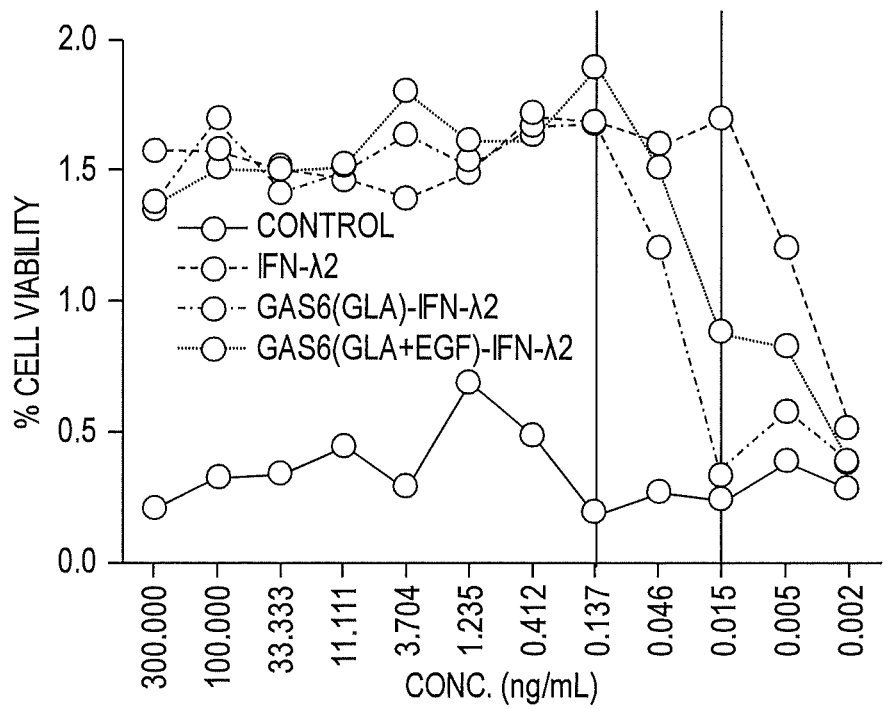
FIG. 20A shows antiviral activity of the fusion molecules equivalent to the recombinant IFN-λ2.
Figure 20B:
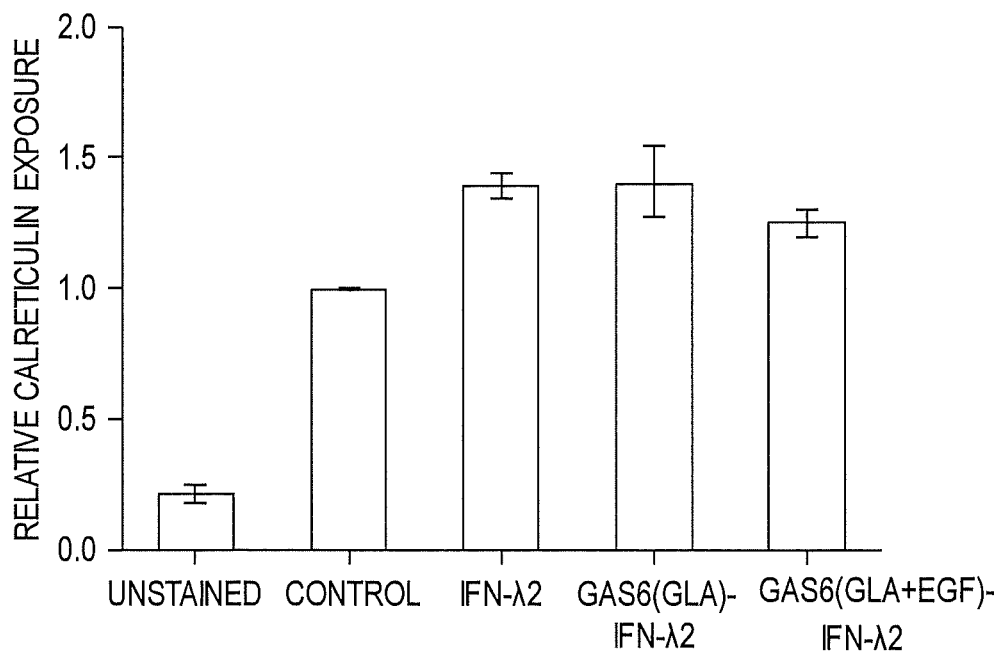
FIGS. 20B and 20C show the expression of immunogenic proteins calreticulin (FIG. 20B) and MHC class I protein (FIG. 20C) as determined by flow cytometry in the ARPE19 cells after treatment with recombinant IFN-λ2 or with fusion molecules of the present invention for 72 hours.
Figure 20C:
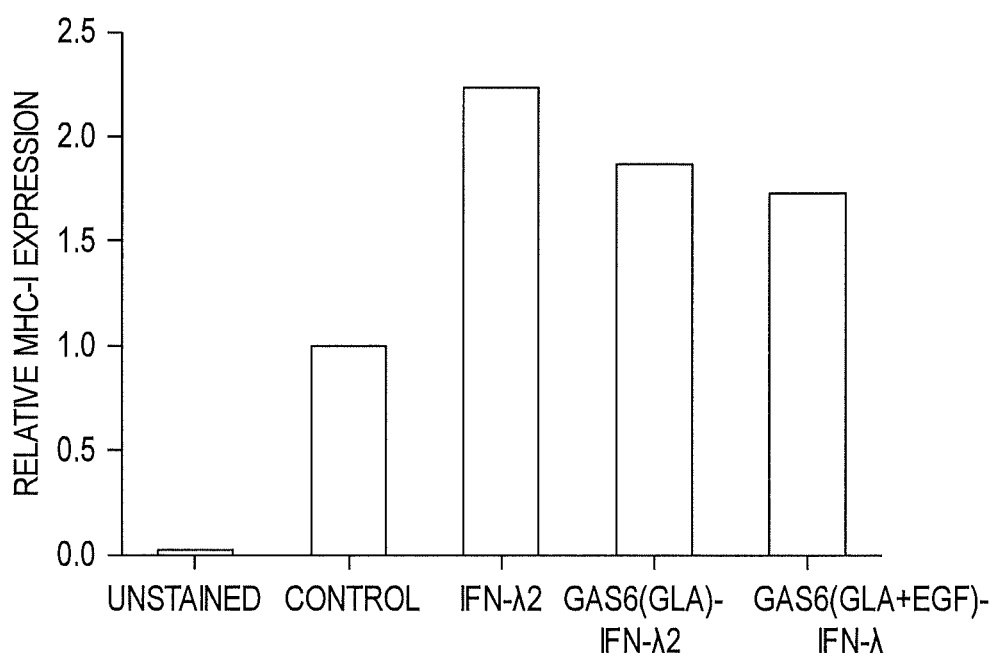

Antiviral activity of the PS-targeting IFN fusion molecules of the present invention were either comparable to the native protein (FIG. 20A; Gas6(Gla)-IFN-λ2 and Gas6(Gla+EGF)—IFN-λ2 versus IFN-λ2) or more potent than acting alone IFN fusion molecules as demonstrated in FIGS. 10 and 11 (Gas6(Gla+EGF)-IFN-β-IFN-λ2 versus IFN-β-IFN-λ2). Further, the ability of the fusion molecules of the present invention to induce an IFN receptor response by inducing expression of immunostimulating proteins calreticulin and MHC class I protein and immunomodulatory PD-L1 protein is depicted in FIGS. 12, 20C, 20B and 13, respectively.

The fusion molecules of the invention can be produced by conventional recombinant expression methodologies using known expression systems including, but not limited to, *E. coli*, yeast, baculovirus, insect, plant or mammalian protein expression systems. The fusion molecule may be recovered and purified from recombinant cell cultures in any effective manner. For example, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. See, e.g., Lin, et al. (1986) *Meth. Enzymol.* 119:183-192. Most preferably, high performance liquid chromatography ("HPLC") is employed for purification. Further methods that may be used for production and isolation of the fusion molecule of the present invention are disclosed in U.S. Pat. No. 6,433,145.

In addition, fusion molecules of the present invention can be chemically synthesized using any effective technique (see, e.g., Creighton (1983) *Proteins: Structures and Molecular Principles*, W.H. Freeman & Co., NY; Hunkapiller, et al. (1984) *Nature* 310:105-111). For example, the fusion molecule or fragments of fusion molecule can be synthesized with a peptide synthesizer.

The invention also encompasses a fusion molecule, which has been modified during or after translation, e.g., by γ-carboxylation, glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH4; acetylation, formylation, oxidation, reduction; metabolic synthesis in the presence of tunicamycin, etc.

Additional post-translational modifications encompassed by the invention include, for example, e.g., γ-carboxylation, N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The fusion molecule may also be modified with a detectable label, such as an enzymatic, fluorescent, isotopic or affinity label to allow for detection and isolation of the protein.

Also provided by the invention are chemically modified derivatives of the fusion molecule of the present invention, which may provide additional advantages such as increased solubility, stability and circulating time of the polypeptide, or decreased immunogenicity (see U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo, et al. (1996) *Appl. Biochem. Biotechnol.* 56:59-72; Vorobjev, et al. (1999) *Nucleosides Nucleotides* 18:2745-2750; and Caliceti, et al. (1999) *Bioconjug. Chem.* 10:638-646.

Polyethylene glycol molecules (or other chemical moieties) should be attached to the fusion molecule with consideration of effects on functional or antigenic domains of the protein. There are a number of attachment methods available to those skilled in the art, see, e.g., EP 0 401 384, which teaches coupling of PEG to G-CSF, and Malik, et al. (1992) *Exp. Hematol.* 20:1028-1035, which describes pegylation of GM-CSF using tresyl chloride. For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a protein via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the fusion molecule of the invention may be accomplished by any number of means. For example, polyethylene glycol may be attached to the protein either directly or by an intervening linker. Linkerless systems for attaching polyethylene glycol to proteins are described in Delgado et al. (1992) Crit. Rev. Thera. Drug Carrier Sys. 9:249-304; Francis, et al. (1998) Intern. J. Hematol. 68:1-18; U.S. Pat. Nos. 4,002,531; 5,349,052; WO 95/06058; and WO 98/32466.

The number of polyethylene glycol moieties attached the fusion molecule of the invention (i.e., the degree of substitution) may also vary. For example, the pegylated protein of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado, et al. (1992) Crit. Rev. Thera. Drug Carrier Sys. 9:249-304.

The fusion molecules of this invention can be used for the treatment of various cancers, viral diseases and other indications, in particular indications where the pathological site is rich in PS.

Accordingly, the present invention also provides pharmaceutical compositions and methods for targeting a cytokine or portion thereof to a pathological site in a subject, inhibiting immunosuppression which occurs from PS recognition by endogenous PS ligands and receptors at a pathological site in a subject, activating one or more cytokine-specific biological activities at a pathological site in a subject, minimizing systemic action of a cytokine in a subject, and/or treating a disease, disorder or condition responsive to cytokine treatment in a subject via administration of an effective amount of the fusion molecule or pharmaceutical composition comprising the fusion molecule to a subject. In one nonlimiting embodiment, the disease, disorder or condition targeted and/or treated with the present invention is cancer, infection or an inflammatory condition or disorder.

For the purposes of the present invention, a "subject" is intended to include a mammal, e.g., a human, non-human primate (e.g., baboon, orangutan, monkey), mouse, pig, cow, goat, cat, rabbit, rat, guinea pig, hamster, horse, monkey, sheep, or other non-human mammal; or a non-mammal, including, e.g., a non-mammalian vertebrate, such as a bird (e.g., a chicken or duck) or a fish, and a non-mammalian invertebrate.

In accordance with the method of the invention, an "effective amount" means a dosage or amount of the fusion molecule or pharmaceutical composition comprising the fusion molecule sufficient to produce a desired result. The desired result may include an objective or subjective improvement in the subject receiving the dosage or amount. In particular, an effective amount is an amount that prevents, ameliorates, reduces, or eliminates one or more signs or symptoms associated with the disease or condition. Treatment can include therapy of an existing condition or prophylaxis of anticipated infections, including but not limited to common recurring infections such as influenza, and circumstances requiring emergency prophylaxis, such as a bioweapon attack.

In some nonlimiting embodiments, the method of the invention is of use in the treatment of chronic and acute viral infections, such as, but not limited to, Chronic Hepatitis C infection, Chronic Hepatitis B infection, herpes virus, papilloma virus, influenza A virus, influenza B virus, respiratory syncytial virus, rhinovirus, coronavirus, rotavirus, norovirus, enterovirus, Zika virus, Ebola virus, Dengue virus, chikungunya virus, hantavirus and AIDS/HIV; cancer, including, but not limited to, solid tumors including sarcomas, carcinomas, and lymphomas of the breast, bone, liver, kidney, lung, neck and throat, skin, colon, prostate, bladder and pancreas; and inflammatory and/or autoimmune conditions or disorders such as, but not limited to, Crohn's Disease, Multiple Sclerosis and arthritis, asthma, psoriasis, dermatitis, autoimmune pulmonary or gastrointestinal inflammation, Condylomata Acuminata. In particular nonlimiting embodiments, the fusion molecules and method of the invention are of use in the treatment of a viral infection or cancer.

Any effective amount of the fusion molecule of the present invention may be administered to a subject in need thereof, e.g., a subject with a disease or condition or at risk of acquiring the disease or condition. As a general proposition, the total pharmaceutically effective amount administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day. If given continuously, the composition is typically administered at a dose rate of about 1 µg/kg/hour to about 50 µg/kg/hour, either by 1-4 injections per day or by continuous subcutaneous infusions, for example, using a mini-pump. An intravenous bag solution may also be employed. The length of treatment needed to observe changes and the interval following treatment for responses to occur may vary depending on the desired effect.

For therapeutic purposes, the fusion molecule of the invention is preferably provided as a pharmaceutical composition containing the fusion molecule in admixture with a pharmaceutically acceptable carrier. The term "pharmaceutical composition" means a composition suitable for pharmaceutical use in a subject, including an animal or human. A pharmaceutical composition generally comprises an effective amount of an active agent and a carrier, including, e.g., a pharmaceutically acceptable carrier such as a non-toxic solid, semisolid or liquid filler, diluent, encapsulating material or formulation auxiliary of any type.

Pharmaceutical compositions containing the fusion molecule of the invention may be administered by any effective route, including, for example, orally, rectally, parenterally, intracisternally, intravaginally, intraperitoneally, topically (as by powders, ointments, drops or transdermal patch), bucally, or as an oral or nasal spray.

The term "parenteral" as used herein refers to any effective parenteral mode of administration, including modes of administration such as intravenous, intramuscular, intraperitoneal, intrasternal, subcutaneous and intraarticular injection and infusion.

The compositions may also suitably be administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman et al. Biopolymers 1983 22:547-556), poly (2-hydroxyethyl methacrylate) (Langer et al. J. Biomed. Mater. Res. 1981 15:167-277; Langer Chem. Tech. 1982 12:98-105), ethylene vinyl acetate or poly-D-(-)-3-hydroxybutyric acid (EP 133, 988).

Sustained-release compositions also include liposomally entrapped polypeptides. Liposomes containing a polypeptide of the present invention are prepared by methods known in the art DE 3,218,121; Epstein, et al. Proc. Natl. Acad. Sci. USA 1985 82:3688-3692; Hwang, et al. Proc. Natl. Acad. Sci. USA 1980 77:4030-4034; EP 52,322; EP 36,676; EP 88,046; EP 143,949; EP 142,641; JP 83-118008; U.S. Pat. Nos. 4,485,045; 4,544,545; and EP 102,324. Ordinarily, the liposomes are of the small (about 200-800 Angstroms), unilamellar type in which the lipid content is greater than about 30 mol. percent cholesterol, the selected proportion being adjusted for effective polypeptide therapy.

When used as an immunooncological (ICI), the fusion molecules of the present invention may be used alone or in combination with other ICIs. In one nonlimiting embodiment, the fusion molecule of the present invention may be used in combination with an anti-PD-1 therapeutic. This combination is particularly attractive, since type I and type III IFNs can induce up-regulation of PD-L1 and this effect may reduce the anti-tumor efficacy of the fusion molecules.

When used as an antiviral, the fusion molecule of the present invention may be administered alone, or in combination with other known anti-viral, immunomodulatory and anti-proliferative therapies, such as IL-2, KDI, Ribavirin and temozolomide.

The invention also provides a pharmaceutical pack or kit including one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the fusion molecule of the present invention may be employed in conjunction with other therapeutic compounds.

The following nonlimiting examples are provided to further illustrate the present invention.

EXAMPLES

Example 1: Methods for Synthesis of the Fusion Molecules

To generate fusion molecules for biological evaluation, HEK293T cells were transiently transfected with mammalian plasmids expressing intact unmodified GAS6, IFN-λ2, IFN-β, and a fusion IFN molecule IFN-β-IFN-λ2 (controls) and six GAS6-IFN fusion molecules, Gas6(Gla)-IFN-λ2, Gas6(Gla)-IFN-β, Gas6(Gla)-IFN-β-IFN-λ2, Gas6(Gla+EGF)-IFN-λ2, Gas6(Gla+EGF)-IFN-β and Gas6(Gla+EGF)-IFN-β-IFN-λ2. Plasmids expressing His-tagged and phosphorylatable versions of the fusion molecules were also created and transfected into HEK293 cells. Conditioned media containing secreted intact or fusion proteins was collected after 48 hours post transfection.

Example 2: Immunoblotting Methods

The condition media containing various intact Gas6 and IFN molecules, as well as Gas6(Gla), or Gas6(Gla+EGF) IFN fusion molecules was resolved by SDS-PAGE, transferred to the membrane and the γ-carboxylation was assessed by immunoblotting with γ-carboxylation and His-tag specific antibodies.

Example 3: Assessing γ-Carboxylation and Cytokine Activity

The activity of the fusion Gas6(Gla), or Gas6(Gla+EGF) IFN fusion proteins was evaluated by treating IFN-λR-γR1 reporter cell line. The reporter cells were treated with recombinant IFN-λ2 used as a control, or HEK293T cell supernatant containing Gas6(Gla) and Gas6(Gla+EGF) IFN fusion molecules with or without apoptotic cells for 30 minutes. Cell lysates were prepared and Stat1 phosphorylation was measured by immunoblotting with antibodies specific for tyrosine phosphorylated Stat1 (pStat1) as a readout for IFN-λ receptor activation. The pStat1 immunoblots showed phosphatidylserine binding dependent enhancement of activation of the IFN-λ receptor by the fusion molecules. Moreover, binding to apoptotic cells of γ-carboxylated Gas6-IFN fusion molecule was demonstrated by co-precipitation of IFN activity with apoptotic cells.

Example 4: Anti-Viral Activity

An equal number of human retinal pigment epithelium ARPE19 cells, or murine intestinal epithelial cells (mIECs) was plated in DMEM media with 10% FCS in all wells of 96 well microtiter plate and treated with recombinant IFN-λ2 at various concentrations ranging from 300 ng/ml to 0.002 ng/ml or with three fold serial dilutions of HEK293T cell supernatant containing Gas6(Gla)-IFN-λ2 and Gas6(Gla+EGF)—IFN-λ2 fusion molecules, or IFN-β-IFN-λ2 and Gas6(Gla+EGF)-IFN-β-IFN-λ2, respectively. After 24 hours of pretreatment, the cells were challenged with vesicular stomatitis virus (VSV) added to the wells at the concentration of 0.1 pfu/cell and the cells were further incubated for 24 hours to analyze the anti-viral activity of the fusion molecules. Cell viability was measured using the MTT assay following manufacturer's protocol (Millipore/Sigma).

ARPE-19 cells or mIECs were also plated in 6 well plates in DMEM media with 10% FCS and were left untreated or treated with recombinant IFN-λ2 (100 ng/ml) or with 1/10 dilution of HEK293T cell supernatant containing Gas6(Gla)-IFN-λ2, Gas6(Gla+EGF)-IFN-λ2, IFN-β-IFN-λ2 or Gas6(Gla+EGF)-IFN-β-IFN-λ2 fusion molecules for 72 hours. Cells were then collected and cell surface levels of MHC class I antigen expression, calreticulin expression or PD-L1 expression were measured by flow cytometry.

Example 5: Anti-Tumor Activity

Immunocompetent syngeneic 6-8 week old C57BL/6 mice (Jackson Laboratory) were injected with $10^5$ EO771 mock cells (EO771 cells transfected with empty vector) IFN-β-IFN-λ2 Gas6(Gla+EGF)-IFN-β,Gas6(Gla+EGF)-IFN-λ2 or Gas6(Gla+EGF)-IFN-β-IFN-λ2 fusion molecule secreting cells (EO771 cells transfected with vectors expressing various fusion molecules) into the mammary fat-pad. Mice were checked for tumor growth by palpation of the injection site every 1 to 2 days and the tumor volume (V) was calculated by measuring tumor length (L) and width (W) using clipper and then applying a formula $V=(L \times W \times W)/2$.

Example 6: Evaluation of the Ability of Fusion Molecule to be Recruited to and Localize in the Tumor Micro-Environment To investigate whether the fusion molecules of the present invention retain the capacity to be recruited to and localize in the tumor micro-environment, an evaluation is performed to determine whether the fusion molecules can be specifically delivered to the tumor site. For these studies, Mx2-luciferase reporter transgenic (TG) mice, described by Pulverer, J. E. et al. (Journal of Virology 2010 84:8626-8638), where the expression of luciferase is controlled by the IFN-inducible Mx2 promoter are used. These reporter mice, when injected intravenously with either type I or type III IFNs express luciferase in tissue-specific manner: type I IFNs induce luciferase expression predominantly in liver, whereas type III IFNs trigger luciferase expression in the gastro-intestinal tract (McElrath, C. et al. Cytokine 2016 87:141-141). His-tagged proteins are produced in HEK293 cells and purified to homogeneity. Intact and fusion IFN proteins are first injected into the reporter mice at various concentrations and the location and the duration of luciferase expression is monitored in live animals with the use of, for example, an Xenogen IVIS 200 Imaging System. Next, female mice are injected into mammary fat-pads with EO771 cells and after the tumors are established, the mice are injected with intact or Gas6 fusion IFN molecules and luciferase expression is evaluated in live animals. Under physiological conditions, uncleared apoptotic cells and PS-positive stressed cells are rarely observed, even in tissues with high rates of cellular turnover such as the thymus and spleen. This is because cells undergoing apoptosis as a part of normal homeostasis are very efficiently and robustly efferocytosed and PS is not detected in healthy tissues. Therefore, the PS-targeting of the fusion molecules of the present invention determined by this study is indicative of localized delivery of the designed fusion molecules to the sites where PS is up-regulated as a part of stress response and cancer, viral infection or inflammation.

Example 7: Evaluation of the Ability of Fusion Molecule to be Recruited to and Localize in the Tumor Micro-Environment and Virus Infection Site Following purification to homogeneity, phosphorylatable IFN fusion molecules are radioactively labeled in vitro and injected through tail-vein or SQ injection into tumor bearing mice and mice infected with either respiratory influenza A virus or gastro-intestinal rotovirus, and the in vivo distribution of the labeled proteins is monitored by x-ray imaging and by measuring radioactivity distribution in various dissected tissues.

Example 8: Anti-Tumor Efficacies of Fusion Molecules in Two Mouse Models

The properties of fusion molecules of the present invention in altering the tumor microenvironment are compared in two independent and genetically amenable orthotopic transplantation models of breast cancer growth. These models include a 4T1 cell model (for the BALB/c mouse strain) and an EO771 cell model (for the C57BL/6 mouse strain). Both models reflect aggressive triple negative tumor breast models that recapitulate aspects of human breast cancer, including a low immunogenic potential and spontaneous metastasis to the lung. Moreover, both 4T1 and EO771 cells are believed to express all three TAMs, making these cancer models suitable to study tumors expressing PS receptors. 4T1 and EO771 cells constitutively expressing various intact or Gas6 fusion IFN molecules have been generated. Cell populations expressing comparable levels of IFN molecules are selected. The growth kinetics of the modified cells is first compared in vitro. For animal studies, 8 week-old syngeneic wild-type C57BL/6 (EO771) or BALB/c (4T1) female virgin mice are injected with $10^5$ murine breast cancer cell lines (re-suspended in 50% Matrigel) centrally in the right #4 inguinal mammary fat pad (n=12 mice/group). The volume of primary tumors is evaluated every other day and recorded. When primary tumors reach 1 $cm^3$ volume, the mice are sacrificed and the lung metastasis is quantified. Lungs, bones, brain and other major organs are weighed and half snap-frozen and half fixed for further biochemical and histological analyses to study proliferation (Ki67), apoptosis (Tunnel), micro-vessels (CD31) and PASR staining. Laser micro-capture techniques will be used if needed to dissect the potential spontaneous metastases and perform biochemical analysis.

Example 9: Assessment of Effects of Fusion Molecule on Immune Cell Frequencies in the TME Examining the subsets of immune cells in the TME and how they are altered by fusion molecules of the present invention offers mechanistic insight into their role in altering immune responses. It is expected that the fusion molecules will reverse inhibitory signals that impinge on host anti-tumor responses and reprogram the TME towards a more immune competitive milieu. To address these issues experimentally, a combination of Nanostring and IHC-based methods are used to probe the cellular frequency of PMNs, DCs, MPhs, NK and T cells in the TME and at the tumor margins. As such, when primary tumors are removed, portions are used to examine the margins by IHC and then enzymatically digested to isolate tumor and tumor-infiltrating cells to profile F4/80+ MPhs, GR1+ neutrophils, CD11+ DCs and T cells, myofibroblasts and endothelial cells (PECAM+ cells). Leukocyte (DCs, MPhs, NKs and T cells) infiltration and DC maturation status at the tumor site by immuno-staining cells followed by FACS analysis (BD LSR II) with specific markers such as CD86 (Alexa 350 labeling) for DCs, F4/80 (Alexa 405 labeling) for MPhs, and CD4+(PE-Cy7 labeling) and CD8+(Alexa 649 labeling) for T cells are also assessed. In addition, tumor-associated cytokines and chemokines are quantified by MSD-cytokine arrays (Meso Scale Diagnostics, Rockville, Md.).

Example 10: Assessment of Therapeutic Effects of Fusion Molecules in Animal Models of Tumor Growth Fusion molecules demonstrating the strongest anti-tumor efficacy in the above-described models will be further tested as anti-cancer therapeutics. For these experiments, the fusion molecule will be produced and purified endotoxin-free with the use of His tag purification techniques in amounts sufficient for animal testing. For these experiments, parental 4T1 and EO771 tumors will be allowed to establish and grow to ~0.3 cm³ volume and animals will be injected intravenously everyday with 1 ug of the selected purified fusion molecule. When effective tumor suppression is achieved, low doses and frequency of administration of the recombinant protein will be also tested.

Example 11: Assessment of Therapeutic Effects of Fusion Molecules in Animal Models of Virus Infection Antiviral potency of PS-targeting IFN fusion molecules is tested using a mouse model of influenza A infection. Potencies are compared with intact IFNs. As a prophylaxis, mice are injected SQ or intranasally (IN) with various doses (0.1, 0.3, 1, 3, 10 µg per adult ~20 mg eight-week old mouse; PBS is used as a control mock treatment) 8 or 24 hours preceding infection of mice with 1 $LD_{50}$ of influenza A virus strain PR8, WSN, Udorn or other strains. Survival and weight loss are monitored daily. In addition, in a separate experiment, viral titers and lung histopathology at days 3, 6, and 9 post infection are assessed. Histopathology is used to assess pathology. IHC staining for viral antigen is used to determine whether treatment has altered the pattern of virus spread. Optimal IFN treatment for enhancing survival post infection is also assessed. In this experiment, the effects of treatment after infection with influenza A virus (1 LD50 strain PR8, WSN, Udorn or other strains) is tested with multiple dosing regimens. As above, mice are treated with IFN fusion molecules, single IFN or their combination injected SQ or intranasally (IN) with various doses (0.1, 0.3, 1, 3, 10 µg per adult ~20 mg eight-week old mouse; PBS will be used as a control mock treatment). Infected mice are treated according to the following schedules: days 1, 3, 5; 1-4; 2, 4, 6; 2-5. Mice are analyzed as above, to gauge antiviral protection as well as disease progression.

Example 12: Evaluation of the Ability of Fusion Molecules to Inhibit Signaling of Intact TAM Ligands Through TAM Receptors TAM reporter cell lines (Tyro3/IFN-γR1, Axl/IFN-γR1 and Mertk/IFN-γR1) are treated with intact γ-carboxylated Gas6 and Prost in the presence or absence of the Gas6-IFN fusion molecules given in excess. The ability of the fusion molecules to block TAM receptor activation by endogenous intact ligands is assessed by measuring reduction in Stat1 activation (pStat1).

What is claimed is:

1. A fusion molecule comprising an interferon or immunostimulatory portion thereof and a polypeptide comprising a N-terminal γ-carboxylated phosphatidylserine (PS)-binding Gla domain of growth arrest-specific gene 6 (GAS6) which targets the fusion molecule to PS on the cell surface and enhances and sustains interferon receptor activation by the interferon or immunostimulatory portion thereof, thereby actively changing immune balance from PS-induced immunosuppression to immunostimulation in an externalized PS concentration-dependent manner.

2. The fusion molecule of claim 1 wherein the polypeptide comprises an epidermal growth factor (EGF)-like domain of GAS6 C-terminal to the Gla domain.

3. The fusion molecule of claim 2 wherein the polypeptide promotes oligomerization of the fusion molecule.

4. The fusion molecule of claim 1 wherein the interferon is selected from interferon-α, interferon-β, interferon-λ1, interferon-λ2, interferon-λ3 or a combination or portion thereof.

5. The fusion molecule of claim 1, further comprising a linker between the interferon or immunostimulatory portion thereof and the polypeptide which targets the fusion molecule to PS.

6. A pharmaceutical composition comprising the fusion molecule of claim 1 and a pharmaceutically acceptable carrier.

7. A method for targeting an interferon or immunostimulatory portion thereof to a PS-rich pathological site in a subject, said method comprising administering to the subject the pharmaceutical composition of claim 6.

8. The method of claim 7 wherein the PS-rich pathological site comprises cancer, infection or inflammation.

9. The method of claim 7 wherein one or more interferon-specific biological activities are activated at the pathological site.

10. The method of claim 7 wherein systemic action of the interferon or immunostimulatory portion thereof is minimized.

* * * * *